(12) United States Patent
Wu

(10) Patent No.: US 8,598,161 B2
(45) Date of Patent: *Dec. 3, 2013

(54) COMPOUNDS FOR THE REDUCTION OF BETA-AMYLOID PRODUCTION

(75) Inventor: Yong-Jin Wu, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/478,238

(22) Filed: May 23, 2012

(65) Prior Publication Data
US 2013/0131049 A1    May 23, 2013

Related U.S. Application Data

(60) Provisional application No. 61/489,440, filed on May 24, 2011.

(51) Int. Cl.
C07D 513/04    (2006.01)
C07D 279/08    (2006.01)

(52) U.S. Cl.
USPC .......................... 514/224.2; 544/48

(58) Field of Classification Search
USPC .......................... 514/224.2; 544/48
See application file for complete search history.

(56) References Cited

U.S. PATENT DOCUMENTS

2010/0093999 A1    4/2010    Motoki et al.

FOREIGN PATENT DOCUMENTS

| EP | 1 942 105 | 7/2008 |
|---|---|---|
| WO | WO 2011/005738 | 1/2011 |

OTHER PUBLICATIONS

Anderson, D.H. et al., "Characterization of β amyloid assemblies in drusen: the deposits associated with aging and age-related macular degeneration," Experimental Eye Research, 78, pp. 243-256 (2004).
Cleary, J.P. et al., "Natural oligomers of the amyloid-β protein specifically disrupt cognitive function," Nature Neuroscience, vol. 8, No. 1, pp. 79-84 (Jan. 2005).
Deramecourt, V. et al., "Biochemical Staging of Synucleinopathy and Amyloid Deposition in Dementia With Lewy Bodies," J. Neuropathol. Exp. Neurol., vol. 65, No. 3, pp. 278-288 (Mar. 2006).
Goldstein, L.E. et al., "Cytosolic β-amyloid deposition and supranuclear cataracts in lenses from people with Alzheimer's disease," The Lancet, vol. 361, pp. 1258-1265 (Apr. 12, 2003).
Grundman, M. et al., "Mild Cognitive Impairment Can Be Distinguished From Alzheimer Disease and Normal Aging for Clinical Trials," Arch. Neurol., vol. 61, pp. 59-66 (Jan. 2004).
Hamilton, R.L. et al., "Alzheimer disease pathology in amyotrophic lateral sclerosis," Acta Neuropathol, 107, pp. 515-522 (2004).

Hussain, I. et al., "Identification of a Novel Aspartic Protease (Asp 2) as β-Secretase," Molecular and Cellular Neuroscience, 14, pp. 419-427 (1999).
Lin, X. et al., "Human aspartic protease memapsin 2 cleaves the β-secretase site of β-amyloid precursor protein," Proceedings of the National Academy of Sciences of the USA, vol. 97, No. 4, pp. 1456-1460, (Feb. 15, 2000).
Loane, D.J. et al., "Amyloid precursor protein secretases as therapeutic targets for traumatic brain injury," Nature Medicine, vol. 15, No. 4, pp. 377-379 (Apr. 2009).
Luo, Y. et al., "Mice deficient in BACE1, the Alzheimer's β-secretase, have normal phenotype and abolished β-amyloid generation," Nature Neuroscience, vol. 4, No. 3, pp. 231-232 (Mar. 2001).
Murphy, M.P. et al., "Inclusion-body myositis and Alzheimer disease: Two sides of the same coin, or different currencies altogether?" Neurology, 66, Suppl 1, pp. S65-S68 (2006).
Neumann, M. et al., "Ubiquitinated TDP-43 in Frontotemporal Lobar Degeneration and Amyotrophic Lateral Sclerosis," Science, vol. 314, pp. 130-133 (2006).
Roberds, S.L. et al., "BACE knockout mice are healthy despite lacking the primary β-secretase activity in brain: Implications for Alzheimer's disease therapeutics," Human Molecular Genetics, vol. 10, No. 12, pp. 1317-1324 (2001).
Selkoe, D.J., "Alzheimer's Disease: Genes, Proteins, and Therapy," Physiological Reviews, vol. 81, No. 2, pp. 741-766 (Apr. 2001).
Sinha, S. et al., "Purification and cloning of amyloid precursor protein β-secretase from human brain," Nature, vol. 402, pp. 537-540 (Dec. 2, 1999).

(Continued)

*Primary Examiner* — San-Ming Hui
*Assistant Examiner* — Kathrien Cruz
(74) *Attorney, Agent, or Firm* — John F. Levis

(57) ABSTRACT

Compounds of formula (I), including pharmaceutically acceptable salts thereof, are set forth herein:

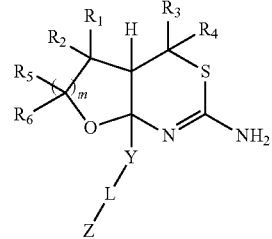

(I)

wherein $R_1$, $R_2$, $R_3$, $R_4$, $R_5$, and $R_6$ are independently hydrogen, $C_1$-$C_6$ alkyl or $C_1$-$C_6$ cycloalkyl;
Y and Z are independently a $C_6$-$C_{10}$-aryl group or a 5-10 membered heterocyclic group, wherein each Y and Z group can be optionally substituted with from 0-3 substituents selected from halogen, amino, $C_{1-4}$alkylamino, $C_{1-4}$dialkylamino, haloC$_{1-4}$ alkyl, OH, CN, $C_1$-$C_6$ alkyl or cycloalkyl, $C_1$-$C_6$ alkoxy, and $C_2$-$C_4$ alkynyl;
L is either a bond or is —NHCO—;
L and Z together can be absent; and
m is 1, 2 or 3.

9 Claims, No Drawings

(56) References Cited

OTHER PUBLICATIONS

Thal, D.R. et al., "Two Types of Sporadic Cerebral Amyloid Angiopathy," Journal of Neuropathology and Experimental Neurology, vol. 61, No. 3, pp. 282-293 (Mar. 2002).

Vassar, R. et al., "β-secretase Cleavage of Alzheimer's Amyloid Precursor Protein by the Transmembrane Aspartic Protease BACE," Science, vol. 286, pp. 735-741 (Oct. 22, 1999).

Walsh, D.M et al., "Deciphering the Molecular Basis of Memory Failure in Alzheimer's Disease," Neuron, vol. 44, pp. 181-193 (Sep. 30, 2004).

Wolfe, M.S., "Secretase Targets for Alzheimer's Disease: Identification and Therapeutic Potential," Journal of Medicinal Chemistry, vol. 44, No. 13, pp. 2039-2060 (Jun. 21, 2001).

Wolfe, M.S. et al., "Intramembrane Proteolysis: Theme and Variations," Science, vol. 305, pp. 1119-1123 (2004).

Yan, R. et al., "Membrane-anchored aspartyl protease with Alzheimer's disease β-secretase activity," Nature, vol. 402, pp. 533-537 (Dec. 2, 1999).

Yokota, O. et al., "NACP/α-Synuclein, NAC, β-amyloid pathology of familiar Alzheimer's disease with the E184D presenilin-1 mutation: a clinicopathological study of two autopsy cases," Acta Neuropathol, 104, pp. 637-648 (2002).

Yoshida, Y. et al., "The potential role of amyloid β in the pathogenesis of age-related macular degeneration," Journal of Clinical Investigation, vol. 115, No. 10, pp. 2793-2800 (Oct. 2005).

"Consensus Recommendations for the Postmortem Diagnosis of Alzheimer's Disease," Neurobiology of Aging, vol. 18, No. S4, pp. S1-S2 (1997).

COMPOUNDS FOR THE REDUCTION OF BETA-AMYLOID PRODUCTION

CROSS REFERENCE TO RELATED APPLICATION

This non-provisional application claims the benefit of U.S. Provisional Application Ser. No. 61/489,440, filed May 24, 2011.

FIELD OF THE INVENTION

The present invention relates to compounds which are inhibitors of β-amyloid peptide (Aβ) production, as well as to methods of treating Alzheimer's Disease (AD) and other conditions related to β-amyloid production using compounds which are inhibitors of β-amyloid peptide (Aβ) production. The invention further relates to pharmaceutical compositions comprising these compounds.

BACKGROUND OF THE INVENTION

Alzheimer's disease (AD) is a progressive neurodegenerative disease which begins with memory loss and progresses to include severe cognitive impairment, altered behavior, and decreased motor function (Grundman, M. et al., *Arch Neurol.* (2004) 61: 59-66; Walsh, D. M. et al., *Neuron* (2004) 44: 181-193). It is the most common form of dementia and represents the third leading cause of death after cardiovascular disorders and cancer. The cost of AD is enormous and includes the suffering of the patients and families and the lost productivity of patients and caregivers. No treatment that effectively prevents AD or reverses the clinical symptoms and underlying pathophysiology is currently available.

A definitive diagnosis of AD for a demented patient requires a histopathological evaluation of the number and localization of neuritic plaques and neurofibrillary tangles upon autopsy (Consensus recommendations for the postmortem diagnosis of Alzheimer's disease. *Neurobiol Aging* (1997) 18: S1-2). Similar alterations are observed in patients with Trisomy 21 (Down syndrome). Plaques primarily consist of β-amyloid (Aβ) peptides that are formed by a stepwise proteolytic cleavage of the amyloid precursor protein (APP) by β-site APP-cleaving enzyme 1 (BACE1), to generate the N-terminus, and γ-secretase, to generate the C-terminus (Selkoe, D. J., *Physiol Rev.* (2001) 81: 741-766). γ-Secretase is a transmembrane protein complex that includes Nicastrin, Aph-1, PEN-2, and either Presenilin-1 (PS-1) or Presenilin-2 (PS-2) (Wolfe, M. S. et al., *Science* (2004) 305: 1119-1123). PS-1 and PS-2 are believed to contain the catalytic sites of γ-secretase. The BACE1 enzyme is a transmembrane aspartyl protease and was described in the literature by several independent groups [see Hussain, I. et al., (1999) *Mol. Cell. Neurosci.,* 14: 419-427; Lin, X. et al., (2000) *Proceedings of the National Academy of Sciences of the United States of America,* 97: 1456-1460; Sinha, S., et al., (1999) *Nature* (London), 402: 537-540; Vassar, R., et al., (1999) *Science* (Washington, D.C.), 286: 735-741; Walsh, D. M. et al., (2002); Wolfe, M. S. (2001); Yan, R. et al., (1999) *Nature* (London), 402: 533-537].

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., *Physiol Rev.,* (2001) 81: 741-766). Current evidence suggests that oligomeric, protofibrillar and intracellular Aβ42 play a significant role in the disease process (Cleary, J. P. et al., *Nat. Neurosci.* (2005) 8: 79-84). Inhibitors of the enzymes that form Aβ42, such as BACE1, represent potential disease-modifying therapeutics for the treatment of AD.

Evidence suggests that a reduction in brain Aβ levels by inhibition of BACE may prevent the onset and progression of AD (Selkoe, D. *Physiol. Rev.* (2001) 81: 741-766; Wolfe, M., *J. Med. Chem.* (2001) 44: 2039-2060). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit BACE1 and reduce production of Aβ could be used to treat these or other Aβ-dependent diseases.

Excess production and/or reduced clearance of Aβ causes CAA (Thal, D. et al., *J. Neuropath. Exp. Neuro.* (2002) 61: 282-293). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that reduce Aβ levels could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., *Acta Neuropathol* (Berl) (2002) 104: 637-648).

Further, sporadic DLB patients have Aβ deposits similar to those in AD (Deramecourt, V. et al., *J Neuropathol Exp Neurol* (2006) 65: 278-288). Based on this data, Aβ likely drives Lewy body pathology in DLB, and therefore compounds that reduce Aβ levels could reduce or prevent DLB.

Approximately 25% of ALS patients have significant dementia or aphasia (Hamilton, R. L. et al., *Acta Neuropathol* (Berl) (2004) 107: 515-522). The majority (~60%) of these patients, designated ALS-D, contain ubiquitin-positive inclusions comprised primarily of the TDP-43 protein (Neumann, M. et al., *Science* (2006) 314: 130-133). About 30% of the ALS-D patients have amyloid plaques consistent with Aβ causing their dementia (Hamilton, R. L. et al., *Acta Neuropathol* (Berl) (2004) 107: 515-522). These patients should be identifiable with amyloid imaging agents and potentially could be treated by compounds that reduce Aβ levels.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., *Neurology* (2006) 66: S65-68). Compounds that reduce Aβ levels could reduce or prevent IBM.

In age-related macular degeneration, Aβ was identified as one of several components of drusen, extracellular deposits beneath the retinal pigment epithelium (RPE) (Anderson, D. H. et al., *Exp Eye Res* (2004) 78: 243-256). A recent study has shown potential links between Aβ and macular degeneration in mice (Yoshida, T. et al., *J Clin Invest* (2005) 115: 2793-2800). Increases in Aβ deposition and supranuclear cataracts have been found in AD patients (Goldstein, L. E. et al., *Lancet* (2003) 361: 1258-1265). Compounds that reduce Aβ levels could reduce or prevent age-related macular degeneration.

A recent study by Georgetown University Medical Center researchers suggests that BACE1 inhibitors may prevent long-term damage from traumatic brain injury (Loane, D. J., et al., *Nature Medicine* (2009) 15: 377-379).

A logical approach to reducing Aβ levels is to block the action of the secretases. The β-secretase enzyme (BACE) is responsible for cleaving APP and forms the amino-terminus of Aβ, initiating the amyloidogenic pathway. Removal of BACE activity in mice by gene targeting completely abolishes Aβ production [see Luo, Y., et al., (2001) *Nature Neuroscience*, 4: 231-232; Roberds, S. L. et al., (2001) *Human Molecular Genetics*, 10: 1317-1324]. BACE –/– mice also show no significant negative phenotypes, suggesting that disruption of BACE-mediated cleavage of APP does not produce additional undesired effects. Thus, compounds that reduce Aβ1-42 production and their pharmaceutical compositions are beneficial agents that will prevent damage from overproduction of Aβ and are useful in treating Alzheimer's disease, Down syndrome, CAA, and inclusion body myositis, DLB, and other disorders where Aβ is overproduced.

PCT Publication WO 2011/005738, published Jan. 13, 2011, sets forth BACE inhibitors.

What is therefore needed in the art are new compounds that inhibit β-amyloid peptide (Aβ) production, as well as compositions containing these compounds, and methods of treatment which utilize these compounds.

SUMMARY OF THE INVENTION

In its first aspect, the present invention provides a compound of formula (I), including pharmaceutically acceptable salts thereof:

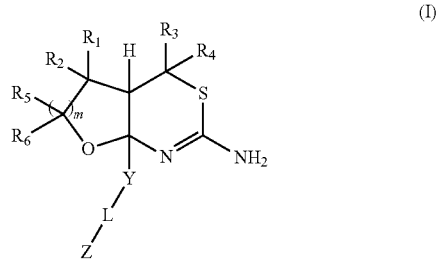

wherein $R_1$, $R_2$, $R_3$, $R_4$, $R_5$, and $R_6$ are independently hydrogen, $C_1$-$C_6$ alkyl or $C_1$-$C_6$ cycloalkyl;

Y and Z are independently a $C_6$-$C_{10}$-aryl group or a 5-10 membered heterocyclic group, wherein each Y and Z group can be further substituted with from 0-3 substituents selected from halogen, amino, $C_{1-4}$alkylamino, $C_{1-4}$dialkylamino, halo$C_{1-4}$ alkyl, OH, CN, $C_1$-$C_6$ alkyl or cycloalkyl, $C_1$-$C_6$ alkoxy, and $C_2$-$C_4$ alkynyl;

L is either a bond or is —NHCO—;

L and Z together can be absent; and m is 1, 2 or 3.

In a second aspect, the present invention provides a pharmaceutical composition for the treatment of disorders responsive to the reduction of β-amyloid peptide production, comprising a therapeutically effective amount of a compound of formula (I), or a pharmaceutically acceptable salt thereof, in association with a pharmaceutically acceptable carrier or diluent.

In a third aspect, the present invention provides a method for the treatment of disorders responsive to the reduction of β-amyloid peptide production in a mammal in need thereof, which comprises administering to said mammal a therapeutically effective amount of a compound of formula (I), or a pharmaceutically acceptable salt thereof. In a first embodiment, said disorder is selected from Alzheimer's Disease (AD), Down Syndrome, mild cognitive impairment (MCI), cerebral amyloid angiopathy (CAA), dementia with Lewy bodies (DLB), amyotrophic lateral sclerosis (ALS-D), inclusion body myositis (IBM), age-related macular degeneration, and cancer. In a second embodiment of the third aspect, said disorder is selected from Alzheimer's Disease and Down Syndrome. In a third embodiment of the third aspect, said disorder is Alzheimer's Disease.

Other aspects of the present invention may include suitable combinations of embodiments disclosed herein.

Yet other aspects and embodiments of the invention may be found in the description provided herein.

DETAILED DESCRIPTION OF THE EMBODIMENTS

The description of the present invention herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule.

All patents, patent applications, and literature references cited in the specification are herein incorporated by reference in their entirety. In the case of inconsistencies, the present disclosure, including definitions, will prevail.

In some instances, the number of carbon atoms in any particular group is denoted before the recitation of the group. For example, the term "halo$C_{1-6}$alkoxy" denotes a haloalkoxy group containing one to six carbon atoms and the term "$C_{1-4}$alkoxy$C_{1-2}$alkyl" denotes an alkoxy group containing one to four alkoxy groups attached to the parent molecular moiety through an alkyl group of one or two carbon atoms. Where these designations exist they supersede all other definitions contained herein.

As used herein and unless otherwise expressly set forth elsewhere in the application, the following terms shall have the following meanings:

The singular forms "a", "an", and "the" include plural reference unless the context clearly dictates otherwise.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylamino," as used herein, refers to —NHR$^x$, wherein R$^x$ is an alkyl group.

The term "alkylaminoalkoxy," as used herein, refers to an alkylamino group attached to the parent molecular moiety through an alkoxy group.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "amino," as used herein, refers to —$NH_2$.

The term "cyano," as used herein, refers to —CN.

The term "cycloalkyl," as used herein, refers to a saturated monocyclic hydrocarbon ring system having three to fourteen carbon atoms and zero heteroatoms.

The term "(cycloalkyl)alkyl," as used herein, refers to an alkyl group substituted with one, two, or three cycloalkyl groups.

The term "cycloalkylamino," as used herein, refers to —$NHR^x$ wherein Rx is a cycloalkyl group.

The term "cycloalkylcarbonyl," as used herein, refers to a cycloalkyl group attached to the parent molecular moiety through a carbonyl group.

The term "dialkylamino," as used herein, refers to —$NR^xR^y$, wherein $R^x$ and $R^y$ are each alkyl groups.

The term "dialkylaminoalkoxy," as used herein, refers to a dialkylamino group attached to the parent molecular moiety through an alkoxy group.

The term "dialkylaminoalkyl," as used herein, refers to an alkyl group substituted with one, two, or three dialkylamino groups.

The term "dialkylaminoalkylcarbonyl," as used herein, refers to a dialkylaminoalkyl group attached to the parent molecular moiety through a carbonyl group.

The term "H", as used herein, refers to hydrogen, including its isotopes.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "Heterocycle," as used herein, refers to a heterocyclic group containing one or more heteroatoms each independently selected form O, S, and N.

The term "hydroxy," as used herein, refers to —OH.

The term "hydroxyalkyl," as used herein, refers to an alkyl group substituted with one, two, or three hydroxy groups.

The term "methylamino," as used herein, refers to —$NHCH_3$.

The term "oxo," as used herein, refers to =O.

It should be understood that the disclosure encompasses all stereochemical forms, or mixtures thereof, which possess the ability to reduce β-amyloid peptide production.

Certain compounds of the present invention may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Certain compounds of the present invention may exist in zwitterionic form and the present disclosure includes each zwitterionic form of these compounds and mixtures thereof.

The compounds of the present invention can also exist as pharmaceutically acceptable salts. The term "pharmaceutically acceptable salt," as used herein, represents salts or zwitterionic forms of the compounds of the present invention which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As set forth above, the present invention provides a compound of formula (I), including pharmaceutically acceptable salts thereof:

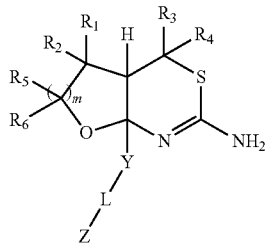

(I)

wherein $R_1$, $R_2$, $R_3$, $R_4$, $R_5$, and $R_6$ are independently hydrogen, $C_1$-$C_6$ alkyl or $C_1$-$C_6$ cycloalkyl;
Y and Z are independently a $C_6$-$C_{10}$-aryl group or a 5-10 membered heterocyclic group, wherein each Y and Z group can be further substituted with from 0-3 substituents selected from halogen, amino, $C_{1-4}$alkylamino, $C_{1-4}$dialkylamino, halo$C_{1-4}$ alkyl, OH, CN, $C_1$-$C_6$ alkyl or cycloalkyl, $C_1$-$C_6$ alkoxy, and $C_2$-$C_4$ alkynyl;
L is either a bond or is —NHCO—;
L and Z together can be absent; and
m is 1, 2 or 3.

More preferably, the compound of formula (I) has $R_1$, $R_2$, $R_3$, $R_4$, $R_5$, and $R_6$ each being independently hydrogen, $C_1$-$C_6$ alkyl or $C_1$-$C_6$ cycloalkyl; Y is phenyl or thiophenyl and Z is a pyridyl, pyrimidinyl or pyrazinyl, wherein each Y and Z group can be optionally substituted with from 0-3 substituents selected from hydrogen, halogen, amino, $C_{1-4}$alkylamino, $C_{1-4}$dialkylamino, halo$C_{1-4}$ alkyl, OH, CN, $C_1$-$C_6$ alkyl or cycloalkyl, $C_1$-$C_6$ alkoxy, or $C_2$-$C_4$ alkynyl; L is either a bond or is —NHCO—; and m is 1 or 2.

In a further embodiment, $R_1$, $R_2$, $R_3$, $R_4$, $R_5$, and $R_6$ are hydrogen;
Y is phenyl and Z is a pyridyl, wherein each Y and Z group can be optionally substituted with from 0-3 halogen substituents and Z can be optionally substituted with from 0-3 halogen, cyano, or $C_2$-$C_4$ alkynyl substituents; L is either a bond or is —NHCO—; and m is 1 or 2.

In another embodiment, $R_1$, $R_2$, $R_3$, $R_4$, $R_5$, and $R_6$ are hydrogen; Y is phenyl optionally substituted with from 0-3 halogen, cyano, or $C_2$-$C_4$ alkynyl substituents; L and Z together can be absent; and m is 1 or 2.

Also preferred are compounds of formula (I) wherein the configuration of the chiral center adjacent to the nitrogen of the aminothiazine is (R), or a pharmaceutically acceptable salt thereof.

Especially preferred are the following compounds of formula (I), including pharmaceutically acceptable salts thereof:
N-(3-((4aR,7aR)-2-amino-4a,5,6,7a-tetrahydro-4H-furo[2,3-d][1,3]thiazin-7a-yl)-4-fluorophenyl)-5-chloropicolinamide;
N-(3-((4aR,7aR)-2-amino-4a,5,6,7a-tetrahydro-4H-furo[2,3-d][1,3]thiazin-7a-yl)-4-cyanophenyl)-5-chloropicolinamide;
N-(3-((4aR,7aR)-2-amino-4a,5,6,7a-tetrahydro-4H-furo[2,3-d][1,3]thiazin-7a-yl)-4-cyanophenyl)-5-bromopicolinamide;
N-(3-((4aR,7aR)-2-amino-4a,5,6,7a-tetrahydro-4H-furo[2,3-d][1,3]thiazin-7a-yl)-4-fluorophenyl)-5-(difluoromethoxy)picolinamide;
N-(3-((4aR,8aR)-2-amino-4,4a,5,6,7,8a-hexahydropyrano[2,3-d][1,3]thiazin-8a-yl)-4-fluorophenyl)-5-(difluoromethoxy)picolinamide;
N-(3-((4aR,8aR)-2-amino-4,4a,5,6,7,8a-hexahydropyrano[2,3-d][1,3]thiazin-8a-yl)-4-fluorophenyl)-5-chloropicolinamide;
N-(3-((4aR,8aR)-2-amino-4,4a,5,6,7,8a-hexahydropyrano[2,3-d][1,3]thiazin-8a-yl)-4-fluorophenyl)-5-bromopicolinamide;
N-(3-((4aR,8aR)-2-amino-4,4a,5,6,7,8a-hexahydropyrano[2,3-d][1,3]thiazin-8a-yl)-4-fluorophenyl)-5-cyanopicolinamide; and
N-(3-((4aR,8aR)-2-amino-4,4a,5,6,7,8a-hexahydropyrano[2,3-d][1,3]thiazin-8a-yl)-4-fluorophenyl)-5-fluoropicolinamide.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the invention further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of formula (I), or a pharmaceutically acceptable salt thereof, with one or more pharmaceutically acceptable carriers, diluents, or excipients.

The dosage of the compounds of Formula I to achieve a therapeutic effect will depend not only on such factors as the age, weight and sex of the patient and mode of administration, but also on the degree of β-AP reduction desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition related to β-AP production as described herein, generally the daily dose will be from about 0.05 mg/kg to about 10 mg/kg and preferably, about 0.1 to 2 mg/kg when administered parenterally. For oral administration, the dose may be in the range from about 0.1 to about 75 mg/kg and preferably from 0.1 to 10 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compounds at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phosphatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The present invention will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments, and are presented to provide what is believed to be the most useful and readily understood description of its procedures and conceptual aspects.

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds may be prepared using the reactions and techniques described in this section. The reactions are performed in solvents appropriate for the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

The abbreviations used in the present application, including particularly in the illustrative schemes and examples which follow, are well-known to those skilled in the art. Some of the abbreviations used are as follows:

Chemical abbreviations used in the specification and Examples are defined as follows: "$(BOC)_2O$" for di-tert-butylpyrocarbonate; dba" for dibenzylideneacetone; "t-Bu" for tert-butyl; "DCM" for dichloromethane; "DIEA" for N,N-diisopropylethylamine; "HATU" for O-(7-Azabenzotriazol-1-yl)-N,N,N',N'-tetramethyluromion hexafluorophosphate; "LDA" for lithium diisopropylamide; "Ph" for phenyl; "TFA" for trifluoracetic acid; "Et" for ethyl; "DMF" for N,N-dimethylformamide; "OAc" for acetate; "h" for hours, "min" for minutes; and "THF" for tetrahydrofuran.

A general synthesis of the compounds of claim 1 is presented below in Scheme 1. Compound 1, wherein X is chloro, bromo or iodo and P1 is a protecting group, is converted to compound 2, where M is lithium or Mg-halide by standard lithium halogen exchange reaction or by treatment with magnesium under thermal conditions (Gregnard reaction). The preferred protecting group is the tert-butyldimethylsilyl group, TBS. Addition of 2 to Weinreb amide 3 furnishes ketone 4 using the conditions described by Weinreb (Tetrahedron Letters, 1981, 22, 3815-3818). Ketone 4 undergoes Michael addition with thiourea to give the adduct 5. The protecting group of compound 5 is removed to give 6 using standard methods (as described in Protecting Groups in Organic Synthesis T. W. Green and PG. M. Wuts, $3^{rd}$ edition, John Wiley & Sons). Cyclization of compound 6 is carried out under acidic conditions to give the cyclized product 7, and the primary amine group of 7 is protected using standard methods (described in Protecting Groups in Organic Synthesis T. W. Green and PG. M. Wuts, $3^{rd}$ edition, John Wiley & Sons) to give compound 8, wherein P2 is a protecting group. The nitro group of 8 is reduced under catalytic hydrogenation conditions to give primary amine 9, and this amine is coupled with acid 10 to give amide 11. Deprotection of 11 using standard methods as described in the reference above affords the compounds 12 of claim 1.

SCHEME 1

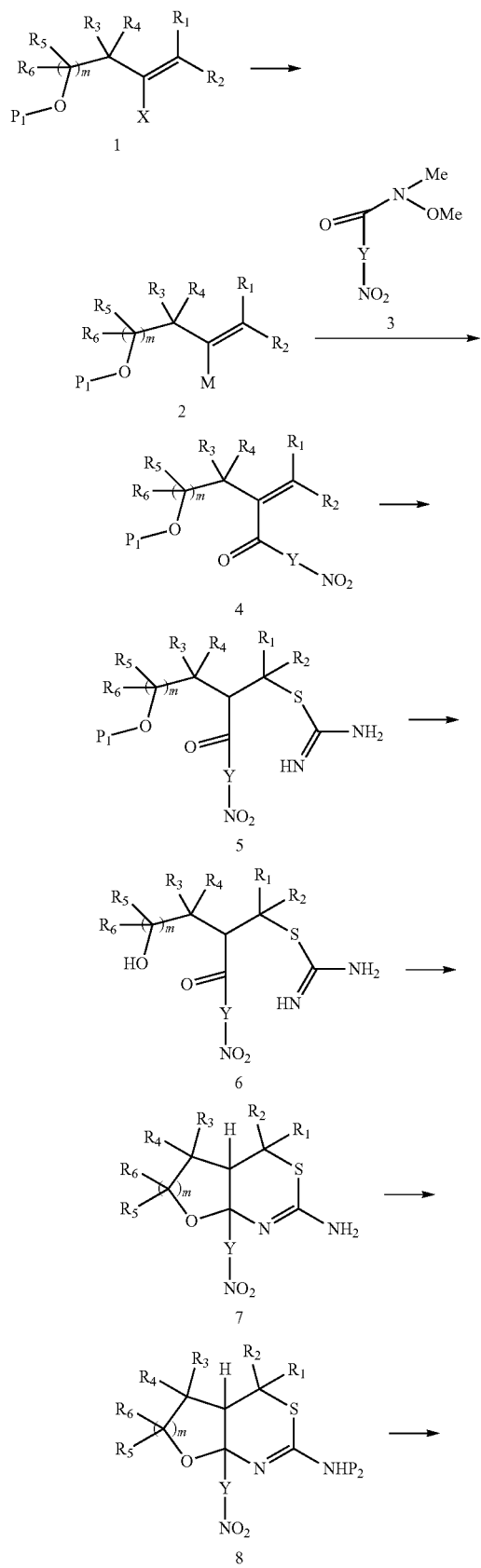

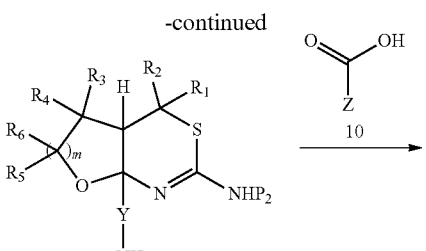

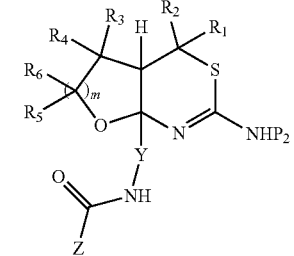

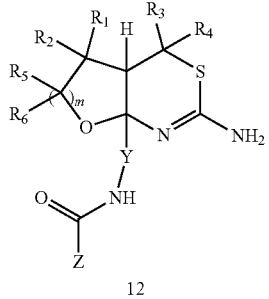

Scheme 2 describes an alternative synthesis of intermediates 4 from compound 2.

Addition of the metal halide 2 to aldehydes 13 provides alcohol 14, and this alcohol is converted to the α,β-unsaturated ketone 4 using either Swern oxidation or using manganese dioxide.

SCHEME 2

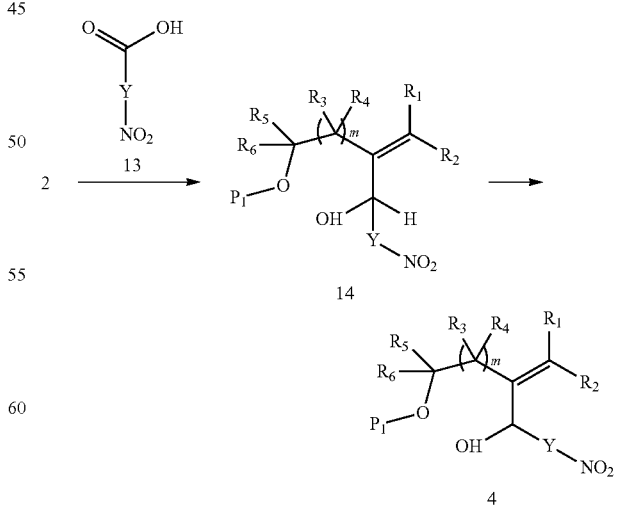

Scheme 3 describes a general synthesis of the compounds of claim 1 wherein ring Y is an optionally substituted phenyl;

$R_1$, $R_2$, $R_3$, $R_4$, $R_5$, $R_6$ are each hydrogen; and L is —NHC(O)—. Vinyl bromide 16 undergoes lithium-halogen exchange using tert-butyllithium to give 17, and this lithium reagent is added to aldehyde 18 at low temperature to give alcohol 19. Alcohol 19 is oxidized either with manganese dioxide or under Swern oxidation conditions to give the α,β-unsaturated ketone 20. Michael addition of this ketone with thiourea proceeds in a polar solvent such as DMF or acetic acid to give the adduct 21. The protecting group of 21 is removed by treatment with tetrabutylammonium fluoride to give primary alcohol 22. Cyclization of this alcohol is carried out with heating under acidic conditions, such as acetic acid, and the resulting primary amine 23 is protected to provide the Boc derivative 24. The nitro group of 24 is reduced via catalytic hydrogenation to afford amine 25, and this amine is coupled with acid 11 to give compound 15. It will be clear that this chemistry can be carried out on optionally substituted aldehydes 18 or using optionally substituted acids 11.

SCHEME 3

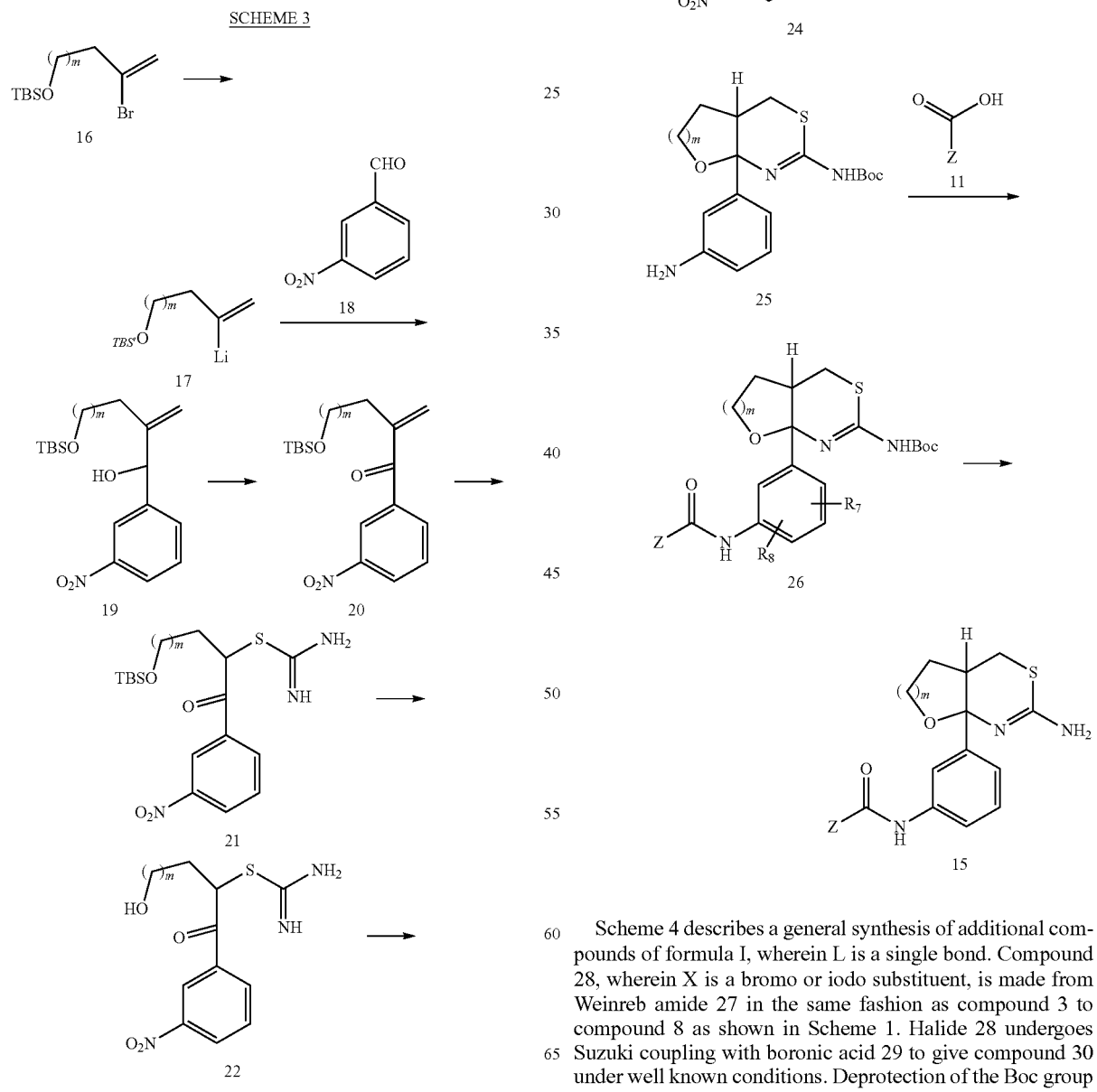

Scheme 4 describes a general synthesis of additional compounds of formula I, wherein L is a single bond. Compound 28, wherein X is a bromo or iodo substituent, is made from Weinreb amide 27 in the same fashion as compound 3 to compound 8 as shown in Scheme 1. Halide 28 undergoes Suzuki coupling with boronic acid 29 to give compound 30 under well known conditions. Deprotection of the Boc group in 30 provides 31.

SCHEME 4

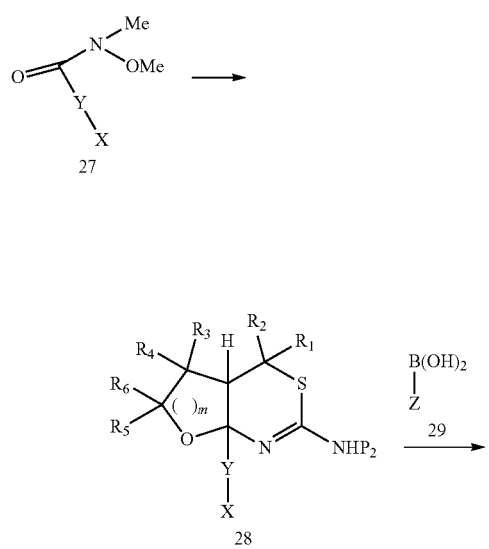

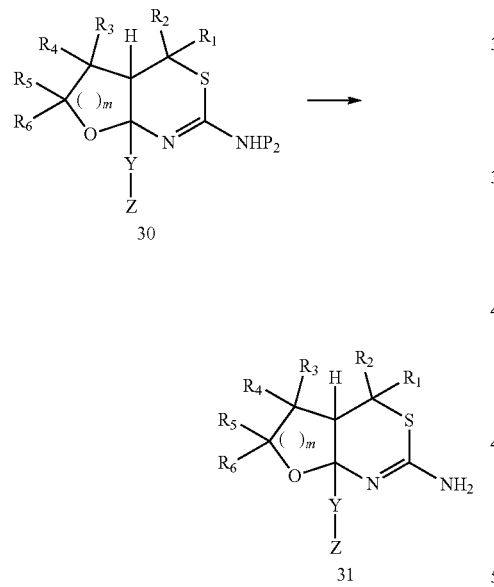

SYNTHESIS OF INTERMEDIATES

Preparation 1

(±)-tert-butyl (4aS,7aS)-7a-(5-(5-bromopicolinamido)-2-fluorophenyl)-4a,5,6,7a-tetrahydro-4H-furo[2,3-d][1,3]thiazin-2-ylcarbamate

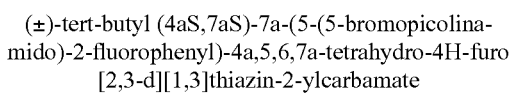

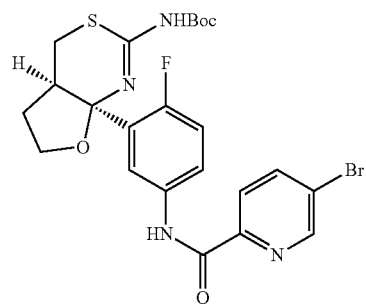
Step A

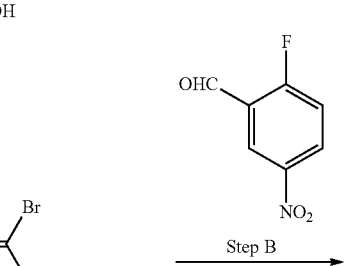
Step B

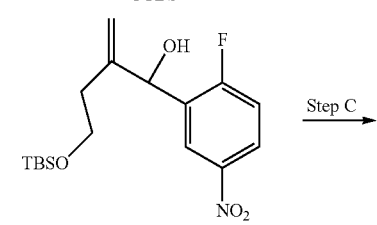
Step C

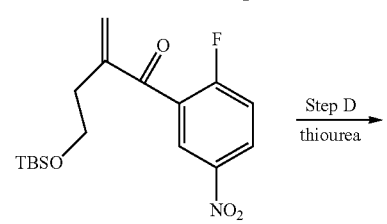
Step D
thiourea

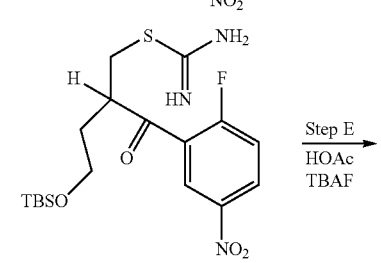
Step E
HOAc
TBAF

"HPLC" is an abbreviation used herein for high pressure liquid chromatography. "MS" refers to mass spectrometry data collected on a high pressure liquid chromatography system with a mass spectrometry detector, and are typically collected using electrospray ionization. "TLC" is an abbreviation used herein for thin layer chromatography. Proton NMR spectra were obtained on a Bruker 400 or 500 spectrometer. Data were referred to the lock solvent.

The examples provided are intended to assist in a further understanding of the present invention. Particular materials employed, species and conditions are intended to further illustrate the specific embodiments of the invention and not limit the reasonable scope thereof.

-continued

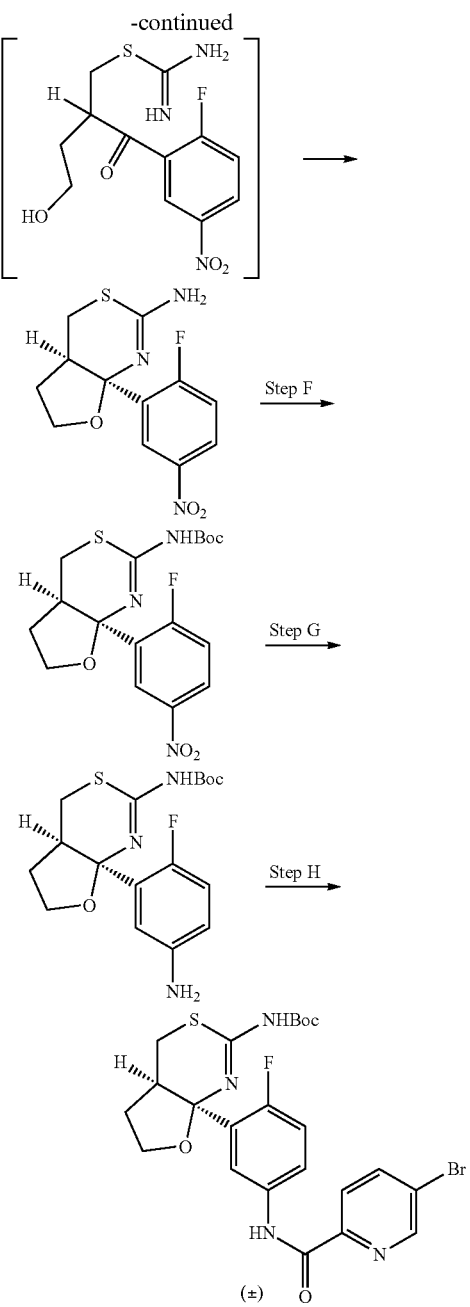

Step A:
(3-bromobut-3-enyloxy)(tert-butyl)dimethylsilane

To a solution of 3-bromobut-3-en-1-ol (5.2 g, 34.4 mmol) in dichloromethane (69 mL) at rt was added tert-Butyldimethylsilyl trifluoromethanesulfonate (10 g. 37.9 mmol) and DIEA (7.22 mL, 41.3 mmol) and the mixture was stirred at rt for 30 min. The reaction mixture was partitioned between dichloromethane and water, and the crude product obtained from the dichloromethane layer was purified by chromatography eluting with 5-30% EtOAc/Hexanes to give the title compound as a colorless liquid (8.72 g, 95%). ¹H NMR (400 MHz, CDCl₃) δ 5.66 (1H, s), 5.48 (1H, s), 3.81 (2H, t, J=6.0 Hz), 2.64 (2H, t, J=6.0 Hz), 0.91 (9H, s), and 0.09 (6H, s).

Step B: 4-(tert-butyldimethylsilyloxy)-1-(2-fluoro-5-nitrophenyl)-2-methylenebutan-1-ol To a solution of (3-bromobut-3-enyloxy)(tert-butyl)dimethylsilane from step A (3.14 g, 11.83 mmol) in THF (10 mL) at −78° C. was added tert-butyllithium (13.91 mL, 23.65 mmol, 1.70 M solution in hexanes) dropwise over a period of 5 min, and the reaction mixture was stirred at −78° C. for 10 min. The resulting lithium reagent was added dropwise to a solution of 2-fluoro-5-nitrobenzaldehyde (2 g, 11.83 mmol) in THF (10 mL) at −78° C., the reaction mixture was stirred at −78° C. for 20 min. The reaction mixture was then partitioned between ethyl acetate and water, and the organic layer was separated and concentrated to a crude product that was purified by chromatography eluting with 0-20% ethyl acetate/hexanes to give a mixture of starting material and the desired product. This mixture was further purified by preparative TLC eluting with 25% EtOAc/hexanes to give the title compound as a colorless oil (941 mg, 22% yield). ¹H NMR (500 MHz, CDCl₃) δ 8.57 (1H, m), 8.18 (1H, m), 7.15 (1H, m), 5.52 (1H, br. s), 5.16 (1H, s), 5.09 (1H, s), 4.96 (1H, m), 3.7-3.9 (2H, m), 2.20-2.35 (2H, m), 0.97 (9H, s), 0.17 (3H) and 0.15 (3H, s).

Step C: 4-(tert-butyldimethylsilyloxy)-1-(2-fluoro-5-nitrophenyl)-2-methylenebutan-1-one To a solution of 4-(tert-butyldimethylsilyloxy)-1-(2-fluoro-5-nitrophenyl)-2-methylenebutan-1-ol (0.94 g, 2.64 mmol) from step B in chloroform (88 mL) was added manganese dioxide (3.45 g, 39.7 mmol), and the reaction mixture was heated under reflux for 24 h. The reaction mixture was filtered through a pad of Celite, and the filtrate was evaporated in vacuo. The residue was purified by chromatography eluting with 5-10% ethyl acetate/hexanes to give the title compound as a colorless oil (0.77 g, 82% yield). Some unreacted starting material was also recovered. ¹H NMR (500 MHz, CDCl₃) δ 8.26 (1H, m), 7.35 (1H, m), 6.18 (1H, s), 5.76 (1H, s), 3.83 (2H, t, J=6.0 Hz), 2.72 (2H, t, J=6.0 Hz), 0.90 (9H, s), and 0.08 (6H, s).

Step D: 4-(tert-butyldimethylsilyloxy)-2-(2-fluoro-5-nitrobenzoyl)butylcarbamimidothioate To a solution of 4-(tert-butyldimethylsilyloxy)-1-(2-fluoro-5-nitrophenyl)-2-methylenebutan-1-one (0.77 g, 2.18 mmol) from step C in acetic acid (8.7 mL) at rt was added thiourea (0.66 g, 8.71 mmol), and the reaction mixture was stirred at rt for 5 h. This crude reaction mixture was used directly for the next step without work-up. MS (M+H)⁺: 430.20.

Step E: (±)-(4aR,7aR)-7a-(2-fluoro-5-nitrophenyl)-4a,5,6,7a-tetrahydro-4H-furo[2,3-d][1,3]thiazin-2-amine To the crude reaction mixture from Step D was added TBAF (1.0 M solution in THF, 3.27 mL, 3.27 mmol), and the reaction mixture was heated at 65° C. for 12 h. The white precipitate was collected by filtration, and the filtrate was directly subjected to HPLC separation eluting with 0-100% A/B (A: 95% H₂O/5% MeCN, 10 MM NH₄OAc; B: 5%

H₂O/95% MeCN, 10 mM NH₄OAC over 30 min period. The product from HPLC separation was combined with the white solid obtained by filtration to provide the title compound (0.82 g). This material contained some unidentified impurities, but was used directly in step F. An analytical sample was obtained by HPLC. $^1$H NMR (500 MHz, CDCl₃) δ 8.56 (1H, m), 8.20 (1H, m), 7.18 (1H, t, J=9.0 Hz), 4.11 (2H, t, J=7.5 Hz), 3.11 (1H, dd, J=4.5, 13.0 Hz), 2.99 (1H, ddd, J=2.0, 8.0, 13.0 Hz), 2.71 (1H, m), 2.20 (2H, m). MS (M+H)$^+$: 298.0.

Step F: (±)-tert-butyl (4aR,7aR)-7a-(2-fluoro-5-nitrophenyl)-4a,5,6,7a-tetrahydro-4H-furo[2,3-d][1,3]thiazin-2-ylcarbamate To a solution of (±)-(4aR,7aR)-7a-(2-fluoro-5-nitrophenyl)-4a,5,6,7a-tetrahydro-4H-furo[2,3-d][1,3]thiazin-2-amine (0.82 g) in dioxane (6.4 mL) was added (BOC)₂O (1.2 g, 5.5 mmol), a saturated sodium bicarbonate solution (6.4 mL), and water (0.9 mL) and the reaction mixture was stirred at rt for 12 h. The reaction was partitioned between ethyl acetate and water, and the ethyl acetate layer was separated and dried to provide a crude product. The sample was purified by chromatography eluting with 0-20% ethyl acetate/hexanes to give the title compound as a white foam (882 mg, 81% yield from Step E). $^1$H NMR (500 MHz, CDCl₃) δ 8.56 8.51 (1H, m), 8.25 (1H, m), 7.24 (1H, t, J=9.0 Hz), 4.14 (2H, t, J=8.5 Hz), 3.23 (1H, m), 2.90 (2H, m), 2.40 (1H, m), 2.20 (1H, m), and 1.50 (9H, s). MS (M+H)$^+$: 398.1.

Step G: (±)-tert-butyl (4aR,7aR)-7a-(5-amino-2-fluorophenyl)-4a,5,6,7a-tetrahydro-4H-furo[2,3-d][1,3]thiazin-2-ylcarbamate To a solution of (±)-tert-butyl (4aR,7aR)-7a-(2-fluoro-5-nitrophenyl)-4a,5,6,7a-tetrahydro-4H-furo[2,3-d][1,3]thiazin-2-ylcarbamate (31 mg, 0.078 mmol) in methanol (3.9 mL) was added 10% Pd/C (17 mg), and the reaction mixture was stirred at rt under a hydrogen atmosphere for 2 h. The reaction mixture was filtered through a pad of Celite and concentrated directly to give the title compound as a colorless oil (30 mg, 99%). $^1$H NMR (500 MHz, CDCl₃) δ 6.87 (2H, m), 6.63 (1H, m), 4.17 (1H, m), 4.09 (1H, m), 3.35 (1H, m), 3.05 (1H, m), 2.89 (1H, m), 2.35 (1H, m), 2.23 (1H, m), and 1.51 (9H, m). MS (M+H)$^+$: 368.2.

Step H: (±)-tert-butyl (4aR,7aR)-7a-(5-(5-bromopicolinamido)-2-fluorophenyl)-4a,5,6,7a-tetrahydro-4H-furo[2,3-d][1,3]thiazin-2-ylcarbamate A solution of (±)-tert-butyl (4aR,7aR)-7a-(5-amino-2-fluorophenyl)-4a,5,6,7a-tetrahydro-4H-furo[2,3-d][1,3]thiazin-2-ylcarbamate (31 mg), 5-bromopicolinic acid (26 mg), HATU (48 mg), and DIEA (44 μL) in DMF (0.41 mL) was stirred at rt for 2 h, and the crude reaction mixture was subjected to preparative HPLC eluting with 0-100% A/B (A: 95% H₂O/5% MeCN, 10 mM NH₄OAc; B: 5% H₂O/95% MeCN, 10 mM NH₄OAC over 12 min period to give the title compound as a yellow foam (32 mg, 68%). $^1$H NMR (500 MHz, CDCl₃) δ 9.89 (1H, s), 8.71 (1H, s), 8.21 (1H, dd, J=0.4, 8.0 Hz), 8.07 (1H, dd, J=2.0, 8.0 Hz), 8.03 (1H, m), 7.72 (1H, m), 7.14 (1H, t, J=10.5 Hz), 4.15 (2H, m), 3.32 (1H, m), 3.03 (1H, m), 2.90 (1H, m), 2.40 (1H, m), 2.22 (1H, m), and 1.51 (9H, s). MS (M+H)$^+$: 553.3.

Preparation 2

(±)-N-(3-((4aR,7aR)-2-amino-4a,5,6,7a-tetrahydro-4H-furo[2,3-d][1,3]thiazin-7a-yl)-4-fluorophenyl)-5-chloropicolinamide

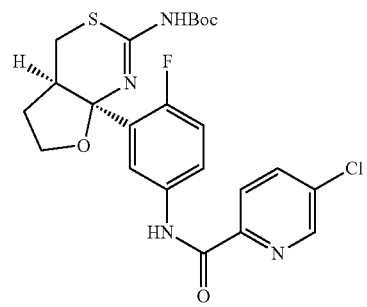 [SMILES: CC(C)(C)OC(=O)NC1=N[C@@]2(c3cc(NC(=O)c4ccc(Cl)cn4)ccc3F)OCC[C@H]2CS1]

A solution of (±)-tert-butyl (4aR,7aR)-7a-(5-amino-2-fluorophenyl)-4a,5,6,7a-tetrahydro-4H-furo[2,3-d][1,3]thiazin-2-ylcarbamate from step G of Preparation 1 (9 mg), 5-chloropicolinic acid (7 mg), HATU (14 mg), and DIEA (11 μL), in DMF (0.12 mL) was stirred at rt for 2 h, and the crude reaction mixture was subjected to preparative HPLC eluting with 0-100% B (A: 95% H₂O/5% MeCN, 10 mM NH₄OAc; B: 5% H₂O/95% MeCN, 10 mM NH₄OAC over 12 min period to give the title compound as a white foam (6 mg, 48%). $^1$H NMR (500 MHz, CDCl₃) δ 9.87 (1H, s), 8.60 (1H, s), 8.26 (1H, d, J=8.5 Hz), 8.02 (1H, br d), 7.92 (1H, dd, J=2.0, 8.0 Hz), 7.72 (1H, m), 7.14 (1H, t, J=10.5 Hz), 4.20 (2H, m), 3.32 (1H, m), 3.02 (1H, m), 2.90 (1H, m), 2.40 (1H, m), 2.24 (1H, m), and 1.51 (9H, s). MS (M+H)$^+$:505.3.

Preparation 3 tert-butyl (4aR,7aR)-7a-(5-(5-cyanopicolinamido)-2-fluorophenyl)-4a,5,6,7a-tetrahydro-4H-furo[2,3-d][1,3]thiazin-2-ylcarbamate

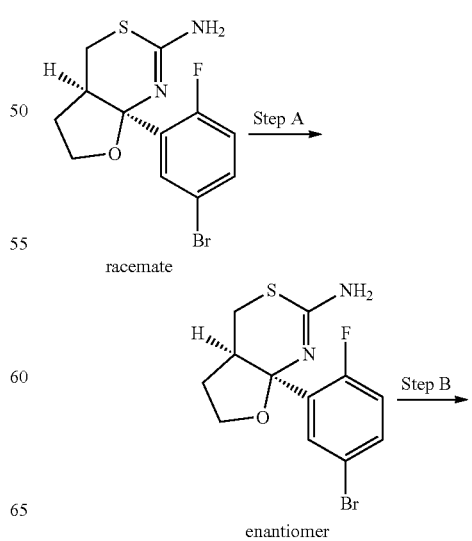

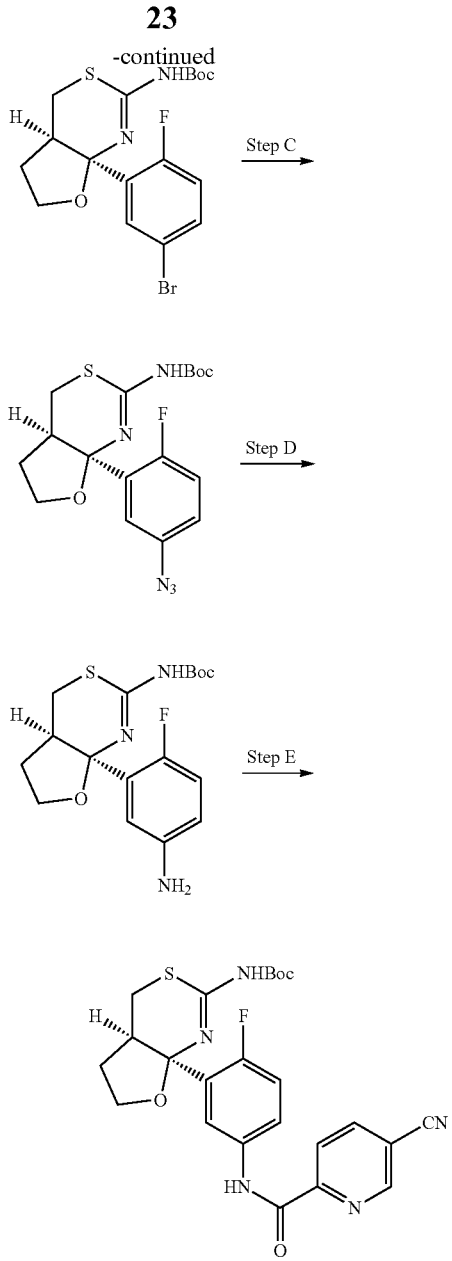

Step A: (4aR,7aR)-7a-(5-bromo-2-fluorophenyl)-4a,5,6,7a-tetrahydro-4H-furo[2,3-d][1,3]thiazin-2-amine (4aR,7aR)-7a-(5-bromo-2-fluorophenyl)-4a,5,6,7a-tetrahydro-4H-furo[2,3-d][1,3]thiazin-2-amine was made from 2-fluoro-5-nitrobenzaldehyde in the same fashion as (±)-(4aR,7aR)-7a-(2-fluoro-5-nitrophenyl)-4a,5,6,7a-tetrahydro-4H-furo[2,3-d][1,3]thiazin-2-amine as shown in Preparation 1. The racemate was purified by chiral HPLC to give tert-butyl (4aR,7aR)-7a-(5-amino-2-fluorophenyl)-4a,5,6,7a-tetrahydro-4H-furo[2,3-d][1,3]thiazin-2-ylcarbamate. $^1$H NMR (400 MHz, CD$_3$SOCD$_3$) δ 7.57 (1H, dd, J=2.4, 6.8 Hz), 7.50 (1H, dt, J=1.2, 6.8 Hz), 7.13 (1H, dd, J=8.4, 11.2 Hz), 6.28 (1H, s), 3.84 (1H, t, J=7.6 Hz), 2.96 (1H, m), 2.86 (1H, m), 2.52 (1H, m), 2.04 (2H, m). MS (M+H)$^+$: 333.0, 335.0

Step B: tert-butyl ((4aR,7aR)-7a-(5-bromo-2-fluorophenyl)-4a,5,6,7a-tetrahydro-4H-furo[2,3-d][1,3]thiazin-2-yl)carbamate To a solution of (4aR,7aR)-7a-(5-bromo-2-fluorophenyl)-4a,5,6,7a-tetrahydro-4H-furo[2,3-d][1,3]thiazin-2-amine (4.8 g, 14.5015 mmol) in 1,4-Dioxane (40 mL) was added di-tert-butyl bicarbonate (6.19 mL, 29.003 mmol) followed by addition of saturated sodium bicarbonate (33.6 mL) and water (4.8 mL) at rt, and the reaction mixture was stirred at rt for 12 h. The reaction mixture was diluted with water (150 mL) and extracted with ethyl acetate (3×100 mL), and the combined organics were dried over the sodium sulphate and concentrated under reduced pressure to give the crude product. The crude product was purified by silica gel column chromatography eluting with 30-40% ethyl acetate-hexanes (combiflash) to give the title compound as a white solid (3.5 g, 56% yield). $^1$H NMR (400 MHz, CDCl$_3$) δ 7.67 (1H, dd, J=2.4, 6.8 Hz), 7.43 (1H, dt, J=1.2, 6.8 Hz), 6.96 (1H, dd, J=8.4, 11.2 Hz), 4.13 (1H, m), 4.03 (1H, m), 3.26 (1H, m), 2.86 (2H, m), 2.36 (1H, m), 2.21 (1H, m), and 1.47 (9H, s). MS (M+H)$^+$:431.0, 435.0

Step C: tert-butyl ((4aR,7aR)-7a-(5-azido-2-fluorophenyl)-4a,5,6,7a-tetrahydro-4H-furo[2,3-d][1,3]thiazin-2-yl)carbamate A suspension of tert-butyl ((4aR,7aR)-7a-(5-bromo-2-fluorophenyl)-4a,5,6,7a-tetrahydro-4H-furo[2,3-d][1,3]thiazin-2-yl)carbamate (300 mg, 0.696 mmol), sodium azide (274 mg, 4.21 mmol), trans-1,2-(bismethylamino)cyclohexane (0.073 mL, 0.464 mmol), 0.66 M aqueous L-ascorbic acid sodium salt (0.780 mL, 0.515 mmol) and 0.33 M aqueous copper(II) sulfate pentahydrate (0.936 mL, 0.309 mmol) in ethanol (3.6 mL) and water (0.70 mL) was heated to 80° C. for 1 h. Water was added and the aqueous layer was extracted with EtOAc (×3). The combined organic layers were washed with brine, dried over anhydrous sodium sulfate, and filtered, and the filtrate was evaporated in vacuo to give the crude product. The crude product was purified by preparative TLC on silica gel (0.50 mm thickness) eluting with 30% EtOAc/Hexane to give tert-butyl ((4aR,7aR)-7a-(5-azido-2-fluorophenyl)-4a,5,6,7a-tetrahydro-4H-furo[2,3-d][1,3]thiazin-2-yl)carbamate (100 mg, 0.254 mmol, 36.5% yield) as a white foam. $^1$H NMR (500 MHz, CHLOROFORM-d) δ 7.30-7.24 (m, 1H), 7.09 (dd, J=10.7, 8.7 Hz, 1H), 7.05-6.93 (m, 1H), 4.23-4.02 (m, 2H), 3.29 (d, J=12.7 Hz, 1H), 2.95 (br. s., 2H), 2.45-2.32 (m, 1H), 2.27-2.15 (m, 1H), 1.50 (s, 9H). MS (M−1): 392.2.

Step D: tert-butyl ((4aR,7aR)-7a-(5-amino-2-fluorophenyl)-4a,5,6,7a-tetrahydro-4H-furo[2,3-d][1,3]thiazin-2-yl)carbamate A suspension of tert-butyl ((4aR,7aR)-7a-(5-azido-2-fluorophenyl)-4a,5,6,7a-tetrahydro-4H-furo[2,3-d][1,3]thiazin-2-yl)carbamate (50 mg, 0.127 mmol), 10% Pd/C (135 mg, 0.127 mmol) in methanol (5525 μL) was stirred under hydrogen balloon at rt for 12 h. The reaction mixture was filtered and the filtrate was evaporated in vacuo to tert-butyl ((4aS,7aS)-7a-(5-amino-2-fluorophenyl)-4a,5,6,7a-tetrahydro-4H-furo[2,3-d][1,3]thiazin-2-yl)carbamate (44 mg, 0.120 mmol, 94% yield) as a yellowish oil. This material was used directly for the next reaction without purification. MS (M+H)+: 368.14.

Step E: tert-butyl ((4aR,7aR)-7a-(5-(5-cyanopicolinamido)-2-fluorophenyl)-4a,5,6,7a-tetrahydro-4H-furo[2,3-d][1,3]thiazin-2-yl)carbamate A solution of 5-cyanopicolinic acid (6.65 mg, 0.045 mmol), tert-butyl ((4aS,7aS)-7a-(5-amino-2-fluorophenyl)-4a,5,6,7a-tetrahydro-4H-furo[2,3-d][1,3]thiazin-2-yl)carbamate (11 mg, 0.030 mmol), HATU (17.07 mg, 0.045 mmol) and Hunig's Base (10.46 µL, 0.060 mmol) in DMF (299 µL) was stirred at rt for 12 h. The crude product was purified by reverse phase preparative HPLC on a Luna C18 column (10 µM, 30×100 mm) eluting with 0-100% B (A: 95% eater/5% MeCN/10 nM NH$_4$OAc, B: 5% water/95% MeCN/10 mM NH$_4$OAc) over 12 min to give tert-butyl ((4aS,7aS)-7a-(5-(5-cyanopicolinamido)-2-fluorophenyl)-4a,5,6,7a-tetrahydro-4H-furo[2,3-d][1,3]thiazin-2-yl)carbamate (6 mg, 0.012 mmol, 40.3% yield) as a white solid. $^1$H NMR (500 MHz, CHLOROFORM-d) δ 9.90 (s, 1H), 8.94 (d, J=1.2 Hz, 1H), 8.45 (d, J=8.1 Hz, 1H), 8.24 (dd, J=8.1, 2.0 Hz, 1H), 8.10-7.97 (m, 1H), 7.72 (d, J=4.0 Hz, 1H), 7.16 (dd, J=10.7, 9.0 Hz, 1H), 4.27-4.06 (m, 2H), 3.32 (d, J=12.7 Hz, 1H), 3.04-2.84 (m, 2H), 2.49-2.34 (m, 1H), 2.23 (td, J=13.0, 7.9 Hz, 1H), 1.51 (s, 9H). MS (M+H)+: 498.20.

A solution of (±)-tert-butyl (4aR,7aR)-7a-(5-amino-2-fluorophenyl)-4a,5,6,7a-tetrahydro-4H-furo[2,3-d][1,3]thiazin-2-ylcarbamate from step G of Preparation 1 (9 mg), 5-cyanopicolinic acid (6 mg), HATU (14 mg), and DIEA (11 µL), in DMF (0.12 mL) was stirred at rt for 2 h, and the crude reaction mixture was subjected to preparative HPLC eluting with 0-100% B (A: 95% H$_2$O/5% MeCN, 10 mM NH$_4$OAc; B: 5% H$_2$O/95% MeCN, 10 mM NH$_4$OAC over 12 min period to give the title compound as a white foam (5 mg, 41%). $^1$H NMR (500 MHz, CDCl$_3$) δ 9.90 (1H, s), 8.94 (1H, s), 8.45 (1H, d, J=8.0 Hz), 8.24 (1H, dd, J=2.0, 8.5 Hz), 8.03 (1H, m), 7.72 (1H, m), 4.10-4.25 (2H, m), 3.32 (1H, m), 3.02 (1H, m), 2.90 (1H, m), 2.42 (1H, m), and 2.23 (1H, m) and 1.51 (9H, s). MS (M+H)+: 498.2.

Preparation 4 tert-butyl (4aR,7aR)-7a-(5-(5-fluoropicolinamido)-2-fluorophenyl)-4a,5,6,7a-tetrahydro-4H-furo[2,3-d][1,3]thiazin-2-ylcarbamate

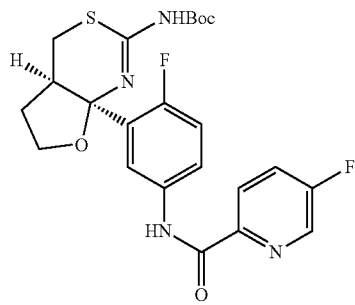 [SMILES: CC(C)(C)OC(=O)NC1=N[C@@]2(c3cc(NC(=O)c4ccc(F)cn4)ccc3F)OCC[C@H]2CS1]

A solution of 5-fluoropicolinic acid (6.34 mg, 0.045 mmol), tert-butyl ((4aR,7aR)-7a-(5-amino-2-fluorophenyl)-4a,5,6,7a-tetrahydro-4H-furo[2,3-d][1,3]thiazin-2-yl)carbamate (11 mg, 0.030 mmol), HATU (17.07 mg, 0.045 mmol), Hunig's Base (10.46 µL, 0.060 mmol) in DMF (299 µL) was stirred at rt for 10 h. The crude reaction mixture was purified by reverse phase preparative HPLC on a Luna C18 column (10 µM, 30×100 mm) eluting with 0-100% B (A: 95% eater/5% MeCN/10 nM NH$_4$OAc, B: 5% water/95% MeCN/10 mM NH$_4$OAc) over 12 min to give tert-butyl ((4aR,7aR)-7a-(2-fluoro-5-(5-fluoropicolinamido)phenyl)-4a,5,6,7a-tetrahydro-4H-furo[2,3-d][1,3]thiazin-2-yl)carbamate (6 mg, 0.012 mmol, 40.9% yield) as a white solid.

$^1$H NMR (500 MHz, CHLOROFORM-d) δ 9.85 (s, 1H), 8.49 (d, J=2.6 Hz, 1H), 8.35 (dd, J=8.7, 4.6 Hz, 1H), 8.06-7.99 (m, 1H), 7.75-7.59 (m, 2H), 7.14 (dd, J=10.8, 8.9 Hz, 1H), 4.26-4.09 (m, 2H), 3.33 (d, J=11.0 Hz, 1H), 3.02 (br. s., 1H), 2.90 (d, J=8.9 Hz, 1H), 2.48-2.35 (m, 1H), 2.28-2.15 (m, 1H), 1.51 (s, 9H). MS (M+H)+: 491.18.

Preparation 5

(±)-tert-butyl (4aR,7aR)-7a-(2-fluoro-5-(picolinamido)phenyl)-4a,5,6,7a-tetrahydro-4H-furo[2,3-d][1, 3]thiazin-2-ylcarbamate

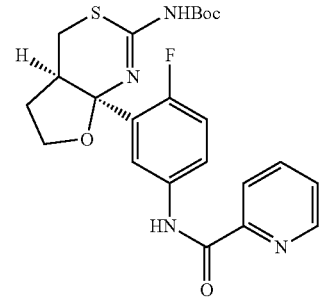 [SMILES: CC(C)(C)OC(=O)NC1=N[C@@]2(c3cc(NC(=O)c4ccccn4)ccc3F)OCC[C@H]2CS1]

A mixture of tert-butyl ((4aR,7aR)-7a-(5-amino-2-fluorophenyl)-4a,5,6,7a-tetrahydro-4H-furo[2,3-d][1,3]thiazin-2-yl)carbamate (step G of Preparation 1, 15 mg, 0.041 mmol), HATU (23.28 mg, 0.061 mmol), and DIEA (14.26 µL, 0.082 mmol) in DMF (136 µL) was stirred at rt for 2 h, and the crude product was purified by prep HPLC (NH4OAc conditions, see Preparation 3) eluting with 0-100% B over 12 min to give tert-butyl ((4aS,7aS)-7a-(2-fluoro-5-(picolinamido)phenyl)-4a,5,6,7a-tetrahydro-4H-furo[2,3-d][1,3]thiazin-2-yl)carbamate (12 mg, 0.025 mmol, 62.2% yield) as a white solid. $^1$H NMR (500 MHz, CHLOROFORM-d) δ 10.08 (s, 1H), 8.66 (d, J=4.6 Hz, 1H), 8.31 (d, J=7.8 Hz, 1H), 8.06 (dt, J=8.4, 3.6 Hz, 1H), 7.94 (td, J=7.7, 1.7 Hz, 1H), 7.70 (d, J=4.3 Hz, 1H), 7.53 (ddd, J=7.5, 4.8, 1.0 Hz, 1H), 7.13 (dd, J=10.8, 9.0 Hz, 1H), 4.23-4.11 (m, 2H), 3.30 (d, J=12.4 Hz, 1H), 3.00 (br. s., 1H), 2.92-2.86 (m, 1H), 2.39 (dd, J=12.6, 7.4 Hz, 1H), 2.26-2.15 (m, 1H), 2.10 (s, 4H), 2.03 (s, 1H), 1.51 (s, 9H).

Preparation 6 tert-butyl ((4aR,7aR)-7a-(5-(5-(difluoromethoxy)picolinamido)-2-fluorophenyl)-4a,5,6,7a-tetrahydro-4H-furo[2,3-d][1,3]thiazin-2-yl)carbamate

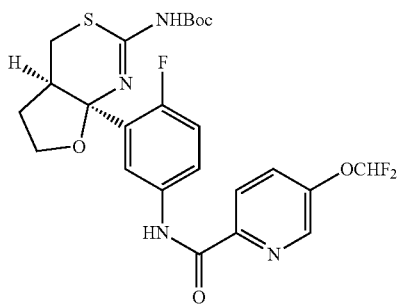 [SMILES: CC(C)(C)OC(=O)NC1=N[C@@]2(c3cc(NC(=O)c4ccc(OC(F)F)cn4)ccc3F)OCC[C@H]2CS1]

A solution of 5-(difluoromethoxy)picolinic acid (8.49 mg, 0.045 mmol), tert-butyl ((4aS,7aS)-7a-(5-amino-2-fluorophenyl)-4a,5,6,7a-tetrahydro-4H-furo[2,3-d][1,3]thiazin-2-yl)carbamate (11 mg, 0.030 mmol), HATU (17.07 mg, 0.045 mmol) and Hunig's Base (10.46 µL, 0.060 mmol) in DMF (299 µL) was stirred at rt for 10 h. The crude product was purified by reverse phase preparative HPLC on a Luna C18 column (10 µM, 30×100 mm) eluting with 0-100% B (A: 95% eater/5% MeCN/10 nM NH₄OAc, B: 5% water/95% MeCN/10 mM NH₄OAc) over 12 min to give tert-butyl ((4aS,7aS)-7a-(5-(5-(difluoromethoxy)picolinamido)-2-fluorophenyl)-4a,5,6,7a-tetrahydro-4H-furo[2,3-d][1,3]thiazin-2-yl)carbamate (6 mg, 0.011 mmol, 37.2% yield) as a white solid. $^1$H NMR (500 MHz, CHLOROFORM-d) δ 9.88 (br. s., 1H), 8.50 (br. s., 1H), 8.34 (d, J=8.7 Hz, 1H), 8.01 (dd, J=9.1, 3.4 Hz, 1H), 7.70 (dd, J=8.6, 2.4 Hz, 2H), 7.19-7.07 (m, 1H), 6.89-6.47 (m, 1H), 4.25-4.07 (m, 2H), 3.33 (d, J=12.7 Hz, 1H), 3.07-2.82 (m, 2H), 2.41 (dd, J=12.8, 7.2 Hz, 1H), 2.29-2.14 (m, 1H), 1.51 (br. s., 9H). MS (M+H)$^+$: 539.22.

Preparation 7 tert-butyl ((4aR,7aR)-7a-(2-fluoro-5-(3-fluoropicolinamido)phenyl)-4a,5,6,7a-tetrahydro-4H-furo[2,3-d][1,3]thiazin-2-yl)carbamate

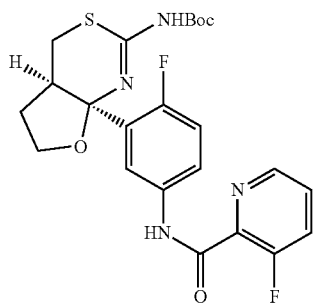 [SMILES: CC(C)(C)OC(=O)NC1=N[C@@]2(c3cc(NC(=O)c4ncccc4F)ccc3F)OCC[C@H]2CS1]

A solution of 3-fluoropicolinic acid (6.34 mg, 0.045 mmol), tert-butyl ((4aS,7aS)-7a-(5-amino-2-fluorophenyl)-4a,5,6,7a-tetrahydro-4H-furo[2,3-d][1,3]thiazin-2-yl)carbamate (11 mg, 0.030 mmol), HATU (17.07 mg, 0.045 mmol), and Hunig's Base (10.46 µL, 0.060 mmol) in DMF (299 µL) was stirred at rt for 10 h. The crude product was purified by reverse phase preparative HPLC on a Luna C18 column (10 µM, 30×100 mm) eluting with 0-100% B (A: 95% eater/5% MeCN/10 nM NH₄OAc, B: 5% water/95% MeCN/10 mM NH₄OAc) over 12 min to give tert-butyl ((4aS,7aS)-7a-(2-fluoro-5-(3-fluoropicolinamido)phenyl)-4a,5,6,7a-tetrahydro-4H-furo[2,3-d][1,3]thiazin-2-yl)carbamate (6 mg, 0.012 mmol, 40.9% yield) as a white solid. $^1$H NMR (500 MHz, CHLOROFORM-d) δ 9.91 (br. s., 1H), 8.49 (br. s., 1H), 8.11-7.97 (m, 1H), 7.71 (d, J=5.2 Hz, 1H), 7.68-7.61 (m, 1H), 7.61-7.55 (m, 1H), 7.17-7.10 (m, 1H), 4.27-4.06 (m, 2H), 3.33 (d, J=13.4 Hz, 1H), 3.03 (d, J=13.7 Hz, 1H), 2.90 (dd, J=13.0, 4.5 Hz, 1H), 2.47-2.33 (m, 1H), 2.29-2.15 (m, 1H), 1.51 (s, 9H). MS (M+H)$^+$: 491.19.

Preparation 8

3-bromo-5-(prop-1-ynyl)pyridine

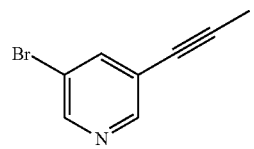

A solution of trimethyl(prop-1-yn-1-yl)silane (1.7 g, 11.48 mmol), 3,5-dibromopyridine (2.72 g, 11.48 mmol), Pd(PPh3)₄ (0.66 g, 0.57 mmol), TBAF (1.0 M solution in THF, 11.48 mL, 11.48 mmol), copper(I) iodide (0.66 g, 3.44 mmol), and triethylamine (5.28 mL, 37.9 mmol) was stirred at rt for 12 h. The reaction mixture was worked up with EtOAc and water, and the crude product was purified by silica gel chromatography eluting with 0-3% EtOAc/Hexanes to give the title compound as a white solid (0.96 g, 42% yield). $^1$H NMR (400 MHz, CHLOROFORM-d) δ 8.55 (dd, J=12.3, 2.0 Hz, 2H), 7.83 (t, J=1.9 Hz, 1H), 2.10 (s, 3H).

Preparation 9

(5-(prop-1-yn-1-yl)pyridin-3-yl)boronic acid

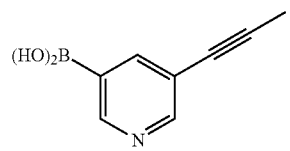

To a solution of 3-bromo-5-(prop-1-ynyl)pyridine (2.96 g, 15.10 mmol) and triisopropyl borate (4.21 ml, 18.12 mmol) in THF and toluene at −40° C. was added n-BuLi (2.5 M solution in hexanes, 7.25 mL, 18.12 mmol) drop wise over a period of 7 min, and the reaction mixture was stirred at −40° C. for 30 min and then warmed up to −20° C. over a period of 8 min. The reaction was quenched with HCl (15.10 ml, 2 M solution, 30.2 mmol), and a reddish solution was formed. The two layers were separated, and the organic layer was extracted with water (3×10 mL). To the combined organic layers were added NaOH (5M solution, 2.416 ml, 12.08 mmol) (to adjust pH to 7). During the addition, a very white cloudy solution was formed. THF (30 mL) was added, but the layers did not separate. Solid sodium chloride was added to make the solution saturated, and the two layers were formed. The layers were separated, and the aqueous layer was extracted with THF (3×20 mL), and the combined THF layers were dried over sodium sulfate and then filtered. The filtrate was evaporated in vacuo, and the residue was concentrated to give a white powder (553 mg). This material was used without further purification.

Preparation 10

(±)-tert-butyl (4aR,7aR)-7a-(2,4-difluoro-5-(5-(prop-1-ynyl)pyridin-3-yl)phenyl)-4a,5,6,7a-tetrahydro-4H-furo[2,3-d][1,3]thiazin-2-ylcarbamate

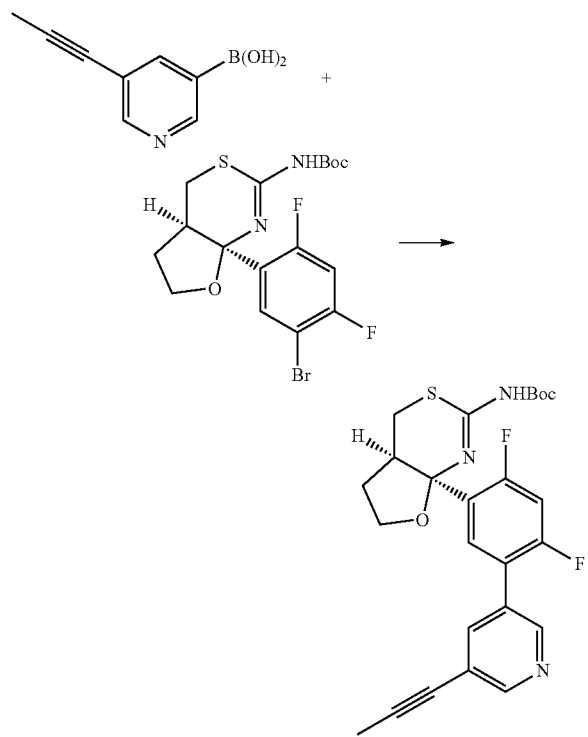

(±)-tert-butyl (4aR,7aR)-7a-(5-bromo-2,4-difluorophenyl)-4a,5,6,7a-tetrahydro-4H-furo[2,3-d][1,3]thiazin-2-ylcarbamate was made from 5-bromo-2,4-difluorobenzaldehyde in the same fashion as (±)-tert-butyl (4aS,7aS)-7a-(2-fluoro-5-nitrophenyl)-4a,5,6,7a-tetrahydro-4H-furo[2,3-d][1,3]thiazin-2-ylcarbamate from 2-fluoro-5-nitrobenzaldehyde (Step A to Step F, Preparation 1). A mixture of (±)-tert-butyl (4aS,7aS)-7a-(5-bromo-2,4-difluorophenyl)-4a,5,6,7a-tetrahydro-4H-furo[2,3-d][1,3]thiazin-2-ylcarbamate (60 mg), 5-(prop-1-ynyl)pyridin-3-ylboronic acid (Preparation 9, 86 mg), cesium carbonate (174 mg), and PdCl$_2$(PPh$_3$)$_2$ (19 mg) in DME (0.44 mL), EtOH (0.22 mL) and water (0.22 mL) was heated at 100° C. for 10 min in a microwave, and the crude reaction mixture was subjected to preparative HPLC eluting with 0-100% B (A: 95% H$_2$O/5% MeCN, 10 mM NH$_4$OAc; B: 5% H$_2$O/95% MeCN, 10 mM NH$_4$OAC over 12 min period to give the title compound as a white foam (22 mg). $^1$H NMR (400 MHz, CHLOROFORM-d) δ 8.65 (br. s., 1H), 7.82 (s, 1H), 7.65 (t, J=8.7 Hz, 1H), 7.00 (t, J=10.3 Hz, 1H), 4.23-4.13 (m, 1H), 4.12-4.04 (m, 1H), 3.30 (d, J=11.5 Hz, 1H), 3.00-2.83 (m, 2H), 2.47-2.35 (m, 1H), 2.28-2.16 (m, 1H), 2.14-2.10 (m, 3H), 1.50 (s, 9H). MS (M+H)$^+$: 486.3.

Preparation 11 tert-butyl ((3aR,7aS)-7a-(5-bromo-2-fluorophenyl)-3,3a,4,7a-tetrahydro-2H-thiopyrano[4,3-b]furan-6-yl)carbamate

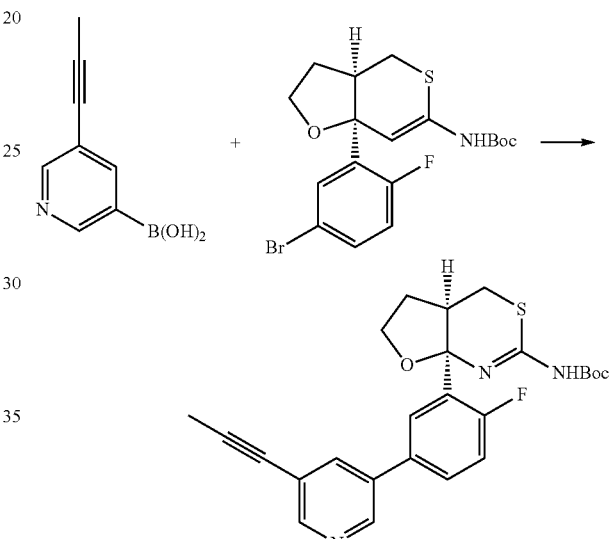

A mixture of (5-(prop-1-yn-1-yl)pyridin-3-yl)boronic acid (Preparation 9, 44.9 mg, 0.279 mmol), tert-butyl ((3aR,7aS)-7a-(5-bromo-2-fluorophenyl)-3,3a,4,7a-tetrahydro-2H-thiopyrano[4,3-b]furan-6-yl)carbamate (Step A of Preparation 3, 60 mg, 0.139 mmol), PdCl$_2$(PPh$_3$)$_2$ (19.57 mg, 0.028 mmol) in DME (465 µL), EtOH (232 µL) and H$_2$O (232 µL) was heated at 90° C. for 5 mM. The crude product was purified by reverse phase preparative HPLC on a Luna C18 column (10 µM, 30×100 mm) eluting with 0-100% B (A: 95% eater/5% MeCN/10 nM NH$_4$OAc, B: 5% water/95% MeCN/10 mM NH$_4$OAc) over 12 min to give a white solid. This solid was purified by preparative TLC on silica gel (0.50 mm thickness) eluting with 50% EtOAc/Hexane to give tert-butyl ((4aS,7aS)-7a-(2-fluoro-5-(5-(prop-1-yn-1-yl)pyridin-3-yl)phenyl)-4a,5,6,7a-tetrahydro-4H-furo[2,3-d][1,3]thiazin-2-yl)carbamate (22 mg, 0.047 mmol, 33.7% yield). $^1$H NMR (500 MHz, CHLOROFORM-d) δ 8.68 (d, J=2.1 Hz, 1H), 8.61 (d, J=1.8 Hz, 1H), 7.83 (t, J=2.1 Hz, 1H), 7.76 (dd, J=7.3, 2.4 Hz, 1H), 7.53 (ddd, J=8.2, 4.4, 2.4 Hz, 1H), 7.20 (dd, J=11.0, 8.4 Hz, 1H), 4.24-4.06 (m, 2H), 3.34 (d, J=12.4 Hz, 1H), 3.01 (br. s., 1H), 2.89 (ddd, J=13.5, 5.5, 1.5 Hz, 1H), 2.48-2.35 (m, 1H), 2.28-2.17 (m, 1H), 2.12 (s, 3H), 1.50 (s, 9H). MS (M+H)$^+$: 468.4.

Preparation 12

(±)-tert-butyl ((4aR,7aR)-7a-(5-(cyclopentylamino)-2-fluorophenyl)-4a,5,6,7a-tetrahydro-4H-furo[2,3-d][1,3]thiazin-2-yl)carbamate

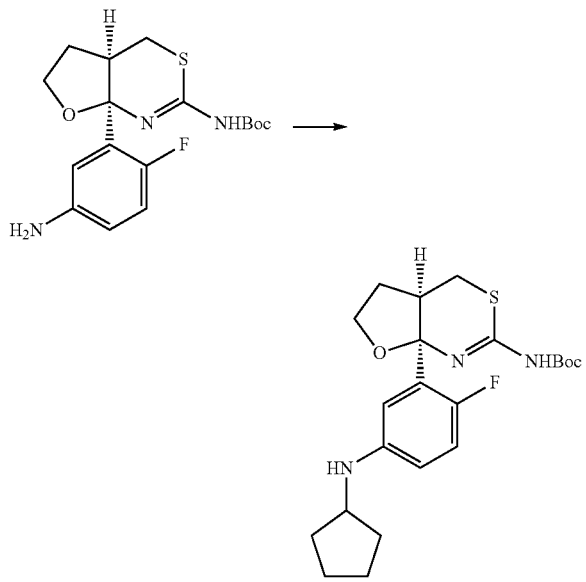 [SMILES: CC(C)(C)OC(=O)NC1=N[C@@]2(c3cc(N)ccc3F)OCC[C@H]2CS1 ; CC(C)(C)OC(=O)NC1=N[C@@]2(c3cc(NC4CCCC4)ccc3F)OCC[C@H]2CS1]

A solution of tert-butyl ((4aS,7aS)-7a-(5-amino-2-fluorophenyl)-4a,5,6,7a-tetrahydro-4H-furo[2,3-d][1,3]thiazin-2-yl)carbamate (Step D, Preparation 3, 32 mg, 0.087 mmol), cyclopentanone (23.38 µL, 0.261 mmol), sodium triacetoxyborohydride (55.4 mg, 0.261 mmol) and acetic acid (14.96 µL, 0.261 mmol) in THF (435 µL) was stirred at rt for 12 h, and LC/MS showed a very clean reaction. The crude reaction mixture was purified by reverse phase preparative HPLC on a Luna C18 column (10 µM, 30×100 mm) eluting with 0-100% B (A: 95% eater/5% MeCN/10 nM NH$_4$OAc, B: 5% water/95% MeCN/10 mM NH$_4$OAc) over 12 min to give tert-butyl ((4aS,7aS)-7a-(5-(cyclopentylamino)-2-fluorophenyl)-4a,5,6,7a-tetrahydro-4H-furo[2,3-d][1,3]thiazin-2-yl)carbamate (16 mg, 0.037 mmol, 42.2% yield) as a white solid. $^1$H NMR (500 MHz, CHLOROFORM-d) δ 6.90 (dd, J=11.1, 8.7 Hz, 1H), 6.74 (dd, J=6.4, 2.9 Hz, 1H), 6.51 (dt, J=8.7, 3.3 Hz, 1H), 4.22-4.14 (m, 1H), 4.04 (q, J=7.9 Hz, 1H), 3.74 (quin, J=6.1 Hz, 1H), 3.31 (dd, J=13.3, 3.1 Hz, 1H), 3.03 (br. s., 1H), 2.84 (dd, J=13.4, 4.3 Hz, 1H), 2.47-2.31 (m, 1H), 2.25-2.15 (m, 1H), 2.09-1.97 (m, 2H), 1.80-1.57 (m, 4H), 1.53-1.43 (m, 2H), and 1.50 (9H, s). MS (M+H)$^+$: 436.3.

Preparation 13

1,5-dibromo-2,4-difluorobenzene

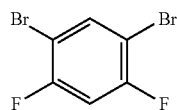

To a solution of 1-bromo-2,4-difluorobenzene (19.3 mL, 171 mmol) in CH$_2$Cl$_2$ (100 mL) was added iron (3.15 g, 56 mmol). To this stirred suspension was added a solution of bromine (11 mL, 214 mmol) in CH$_2$Cl$_2$ (25 mL) drop wise over 30 min. The resulting mixture was stirred at rt overnight. The reaction mixture was slowly poured into saturated aqueous Na$_2$S$_2$O$_3$ (200 mL), and the resulting mixture was stirred at rt for 30 min. This was extracted with CH$_2$Cl$_2$ (3×80 mL). The combined extracts were washed with brine, dried over MgSO$_4$, filtered and concentrated in vacuo to give 1,5-dibromo-2,4-difluorobenzene (40 g, 86% yield) as a brown oil. $^1$H NMR (500 MHz, CHLOROFORM-d) δ 7.79 (t, J=7.0 Hz, 1H), 7.00 (t, J=8.2 Hz, 1H).

Preparation 14

5-bromo-2,4-difluorobenzaldehyde

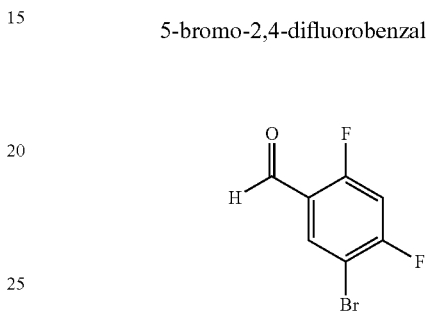

To a solution of 1,5-dibromo-2,4-difluorobenzene (17.5 g, 64.2 mmol) in ether (100 mL) at −78° C. was added n-BuLi (2.5 M solution, 30.8 mL, 77 mmol) over a period of 5 min, and the reaction mixture was stirred at −78° C. for 30 min. Then DMF (9.94 mL, 148 mmol) was added in one portion, and the mixture was stirred at −78° C. for 30 min. The reaction mixture was worked up with EtOAc/sat. NH$_4$Cl, and the crude product was purified by silica gel chromatography eluting with 0-10% EtOAc/Hexanes to give the title compound as a slightly yellow oil (8.5 g, 60% yield). $^1$H NMR (400 MHz, CHLOROFORM-d) δ 10.26 (s, 1H), 8.14 (t, J=7.5 Hz, 1H), 7.05 (dd, J=9.8, 8.0 Hz, 1H).

Preparation 15

2,4-difluoro-5-(pyrimidin-5-yl)benzaldehyde

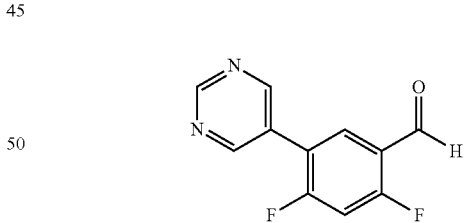

A mixture of bis(triphenylphosphine)palladium(II) chloride (0.56 g, 0.80 mmol), pyrimidin-5-ylboronic acid (0.99 g, 8.0 mmol), 5-bromo-2,4-difluorobenzaldehyde (0.88 g, 3.98 mmol), cesium carbonate (2.59 g, 7.96 mmol) in DME (13 mL), EtOH (7 mL) and water (7 mL) was heated at 100° C. for 45 min, and the crude reaction mixture was subjected to HPLC separation eluting with 0-100% A/B (A: 95% H$_2$O/5% MeCN, 10 MM NH$_4$OAc; B: 5% H$_2$O/95% MeCN, 10 mM NH$_4$OAC over 30 min period to give the title compound as a white solid (450 mg, 51% yield). $^1$H NMR (500 MHz, CHLOROFORM-d) δ 10.40-10.33 (m, 1H), 9.28 (s, 1H), 8.94 (d, J=1.2 Hz, 2H), 8.06 (dd, J=8.4, 7.8 Hz, 1H), 7.15 (t, J=9.9 Hz, 1H), 10.37 (s, 1H).

Preparation 16

5-((tert-butyldimethylsilyl)oxy)-1-(2,4-difluoro-5-(pyrimidin-5-yl)phenyl)-2-methylenepentan-1-one

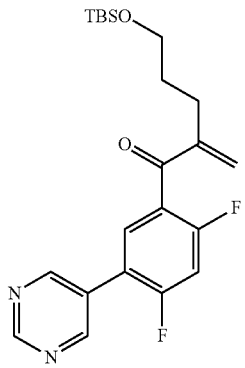 [SMILES: C=C(CCCO[Si](C)(C)C(C)(C)C)C(=O)c1cc(-c2cncnc2)c(F)cc1F]

A solution of ((4-bromopent-4-en-1-yl)oxy)(tert-butyl)dimethylsilane (prepared following the procedures of Rostami, Organic Letters, 2007), 9(4), 703-706) (3.30 g, 11.81 mmol) in THF (25 mL) was added to a flask filled with magnesium (0.574 g, 23.62 mmol) and iodine (0.092 g, 0.363 mmol), and the resulting dark brown suspension was stirred at rt for 15 min and then heated under reflux for 45 min. The color changed from brown to deep reddish and the color of iodine faded 10 min under reflux. Eventually, the color of the reaction mixture turned to grey. This regent was cooled to rt and then added to a suspension of 2,4-difluoro-5-(pyrimidin-5-yl)benzaldehyde (Preparation 15, 2 g, 9.08 mmol) in THF (14 mL), and the reaction mixture was stirred at rt for 12 h. Water was added and the aqueous layer was extracted with EtOAc (×3). The combined organic layers were washed with brine, dried over anhydrous sodium sulfate, and filtered, and the filtrate was evaporated in vacuo to give the crude product. The crude product was purified by silica gel chromatography eluting with 0-35% EtOAc/Hexane to give 5-((tert-butyldimethylsilyl)oxy)-1-(2,4-difluoro-5-(pyrimidin-5-yl)phenyl)-2-methylenepentan-1-one (0.95 g, 2.270 mmol, 24.99% yield). $^1$H NMR (500 MHz, CHLOROFORM-d) δ 9.27 (s, 1H), 8.93 (d, J=1.4 Hz, 2H), 7.59 (dd, J=8.2, 7.3 Hz, 1H), 7.20-7.03 (m, 1H), 6.04 (s, 1H), 5.78 (d, J=1.8 Hz, 1H), 3.70 (t, J=6.3 Hz, 2H), 2.62-2.41 (m, 2H), 1.85-1.70 (m, 2H), 0.93 (m, 9H), 0.09 (m, 6H).

EXAMPLES

The following examples set forth certain specific aspects of the invention, but should not be construed as limiting the scope thereof:

Example 1

N-(3-((4aR,7aR)-2-amino-4a,5,6,7a-tetrahydro-4H-furo[2,3-d][1,3]thiazin-7a-yl)-4-fluorophenyl)-5-bromopicolinamide

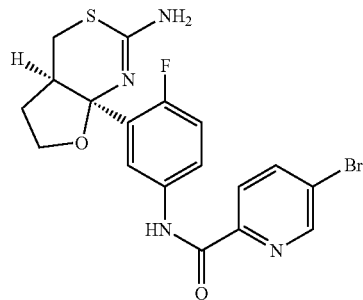 [SMILES: NC1=N[C@@]2(c3cc(NC(=O)c4ccc(Br)cn4)ccc3F)OCC[C@H]2CS1]

The racemic mixture of tert-butyl (4aR,7aR)-7a-(5-(5-bromopicolinamido)-2-fluorophenyl)-4a,5,6,7a-tetrahydro-4H-furo[2,3-d][1,3]thiazin-2-ylcarbamate (Preparation A, 30 mg) was subjected to chiral HPLC (chiralcel OD 21×250 mm, flow rate: 15 mL/min)) eluting with 25% B (A: 0.1% Et$_2$NH/Heptane; B: ethanol) over 30 min to give tert-butyl (4aR,7aR)-7a-(5-(5-bromopicolinamido)-2-fluorophenyl)-4a,5,6,7a-tetrahydro-4H-furo[2,3-d][1,3]thiazin-2-ylcarbamate as a white solid (13 mg, retention time: 12.34 min).

To a solution of tert-butyl (4aR,7aR)-7a-(5-(5-bromopicolinamido)-2-fluorophenyl)-4a,5,6,7a-tetrahydro-4H-furo[2,3-d][1,3]thiazin-2-ylcarbamate (12 mg) in dichloromethane (0.43 mL) was added TFA (67 μL) and the reaction mixture was stirred at rt for 2 h. The reaction mixture was subjected directly to preparative TLC eluting with 90% CH$_2$Cl$_2$/9% MeOH/1% NH$_4$OH to give N-(3- (4aS,7aS)-2-amino-4a,5,6,7a-tetrahydro-4H-furo[2,3-d][1,3]thiazin-7a-yl)-4-fluorophenyl)-5-bromopicolinamide as a white foam (10 mg). $^1$H NMR (500 MHz, CDCl$_3$) δ 9.89 (1H, s), 8.70 (1H, d, J=2.0 Hz), 8.20 (1H, d, J=8.5 Hz), 8.06 (1H, dd, J=2.0, 8.06 Hz), 8.0 (1H, m), 7.75 (1H, m), 7.09 (1H, m), 4.13 (2H, m), 3.22 (1H, m), 3.02 (1H, m), 2.89 (1H, m), and 2.22 (2H, q, J=7.5 Hz). MS: 453.3 (M+H)$^+$. Retention time: 22.49 chiralcel OJ-H 4.6×100 mm, flow rate: 2 mL/min) eluting with 30% B (A: 0.1% Et$_2$NH/Heptane; B: ethanol); Retention time: 12.54 chiralcel OD-H 4.6×100 mm, flow rate: 2 mL/min) eluting with 30% B (A: 0.1% Et$_2$NH/Heptane; B: ethanol).

Example 2

N-(3-((4aR,7aR)-2-amino-4a,5,6,7a-tetrahydro-4H-furo[2,3-d][1,3]thiazin-7a-yl)-4-fluorophenyl)-5-chloropicolinamide

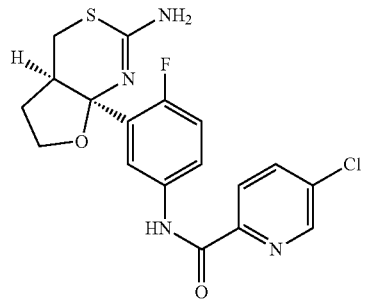 [SMILES: NC1=N[C@@]2(c3cc(NC(=O)c4ccc(Cl)cn4)ccc3F)OCC[C@H]2CS1]

The racemic mixture of tert-butyl (4aR,7aR)-7a-(5-(5-chloropicolinamido)-2-fluorophenyl)-4a,5,6,7a-tetrahydro-4H-furo[2,3-d][1,3]thiazin-2-ylcarbamate (Preparation 2, 150 mg) was subjected to chiral HPLC (chiralcel OD 21×250 mm, flow rate: 15 mL/min)) eluting with 25% B (A: 0.1% Et$_2$NH/Heptane; B: ethanol) over 30 min to give tert-butyl (4aR,7aR)-7a-(5-(5-chloropicolinamido)-2-fluorophenyl)-4a,5,6,7a-tetrahydro-4H-furo[2,3-d][1,3]thiazin-2-ylcarbamate as a white solid (47 mg, retention time: 11.62 min).

A solution of tert-butyl (4aR,7aR)-7a-(5-(5-bromopicolinamido)-2-fluorophenyl)-4a,5,6,7a-tetrahydro-4H-furo[2,3-d][1,3]thiazin-2-ylcarbamate (45 mg) in dichloromethane (0.44 mL) was added TFA (103 μL) and the reaction mixture was stirred at rt for 2 h. The reaction mixture was subjected directly to preparative TLC eluting with 90% CH$_2$Cl$_2$/9% MeOH/1% NH$_4$OH to give N-(3-((4aR,7aR)-2-amino-4a,5,6,7a-tetrahydro-4H-furo[2,3-d][1,3]thiazin-7a-yl)-4-fluorophenyl)-5-chloropicolinamide as a white foam (29 mg). $^1$H NMR (500 MHz, CDCl$_3$) δ 9.89 (1H, s), 8.70 (1H, d, J=2.0

Hz), 8.20 (1H, d, J=8.5 Hz), 8.06 (1H, dd, J=2.0, 8.06 Hz), 8.0 (1H, m), 7.75 (1H, m), 7.09 (1H, m), 4.13 (2H, m), 3.22 (1H, m), 3.02 (1H, m), 2.89 (1H, m), and 2.22 (2H, q, J=7.5 Hz). MS (M+H)$^+$: 453.3. Retention time: 18.96 chiralcel OJ-H 4.6×100 mm, flow rate: 2 mL/min eluting with 30% B (A: 0.1% Et$_2$NH/Heptane; B: ethanol); Retention time: 11.49 chiralcel OD-H 4.6×100 mm, flow rate: 2 mL/min eluting with 30% B (A: 0.1% Et$_2$NH/Heptane; B: ethanol).

Example 3

N-(3-((4aR,7aR)-2-amino-4a,5,6,7a-tetrahydro-4H-furo[2,3-d][1,3]thiazin-7a-yl)-4-fluorophenyl)-5-cyanopicolinamide

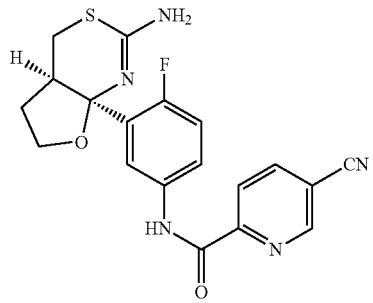 [SMILES: N#Cc1ccc(C(=O)Nc2ccc(F)c([C@@]34N=C(N)SC[C@@H]3CCO4)c2)nc1]

A solution of tert-butyl ((4aR,7aR)-7a-(5-(5-cyanopicolinamido)-2-fluorophenyl)-4a,5,6,7a-tetrahydro-4H-furo[2,3-d][1,3]thiazin-2-yl)carbamate (6 mg, 0.012 mmol) and TFA (18.58 μL, 0.241 mmol) in DCM (121 μL) was stirred at rt for 3 h. The solvents were removed to give N-(3-((4aR,7aR)-2-amino-4a,5,6,7a-tetrahydro-4H-furo[2,3-d][1,3]thiazin-7a-yl)-4-fluorophenyl)-5-cyanopicolinamide (7 mg) as its TFA salt as a colorless oil. $^1$H NMR (500 MHz, CD$_3$OD) δ 9.07 (1H, s), 8.46 (1H, dd, J=2.0, 8.0 Hz0, 8.37 (1H, d, J=8.0 Hz0, 8.17 (1H, dd, J=3.0, 7.5 Hz), 7.93 (1H, m), 7.25 (1H, dd, J=9.0, 11.0 Hz), 4.23 (2H, m), 3.43 (1H, m), 3.29 (1H, m), 3.15 (1H, m), and 2.31 (2H, m). MS (M+H)$^+$: 398.1.

Example 4

(±)-N-(3-((4aR,7aR)-2-amino-4a,5,6,7a-tetrahydro-4H-furo[2,3-d][1,3]thiazin-7a-yl)-4-fluorophenyl)-5-fluoropicolinamide

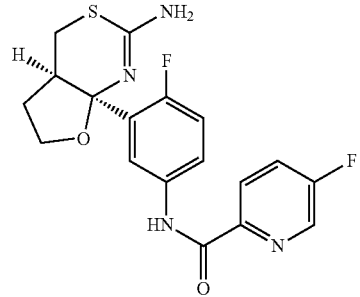 [SMILES: NC1=N[C@@]2(c3cc(NC(=O)c4ccc(F)cn4)ccc3F)OCC[C@H]2CS1]

A solution of tert-butyl ((4aR,7aR)-7a-(2-fluoro-5-(5-fluoropicolinamido)phenyl)-4a,5,6,7a-tetrahydro-4H-furo[2,3-d][1,3]thiazin-2-yl)carbamate (6 mg, 0.012 mmol) and TFA (18.85 μL, 0.245 mmol) in DCM (122 μL) was stirred at rt for 3 h. The solvents were removed to give N-(3-((4aR,7aR)-2-amino-4a,5,6,7a-tetrahydro-4H-furo[2,3-d][1,3]thiazin-7a-yl)-4-fluorophenyl)-5-fluoropicolinamide (7 mg) as its TFA salt. $^1$H NMR (500 MHz, CHLOROFORM-d) δ 9.83 (s, 1H), 8.48 (d, J=2.7 Hz, 1H), 8.35 (dd, J=8.7, 4.6 Hz, 1H), 8.00-7.96 (m, 1H), 7.70 (dd, J=6.9, 2.7 Hz, 1H), 7.62 (td, J=8.3, 2.7 Hz, 1H), 7.08 (dd, J=10.9, 8.8 Hz, 1H), 4.11 (t, J=7.2 Hz, 3H), 3.16 (dd, J=13.0, 4.0 Hz, 1H), 2.98 (ddd, J=12.9, 7.5, 1.8 Hz, 1H), 2.78 (dd, J=7.1, 4.0 Hz, 1H), 2.22-1.99 (m, 2H). MS (M+H)$^+$: 391.2.

Example 5

(±)-N-(3-((4aR,7aR)-2-amino-4a,5,6,7a-tetrahydro-4H-furo[2,3-d][1,3]thiazin-7a-yl)-4-fluorophenyl)picolinamide

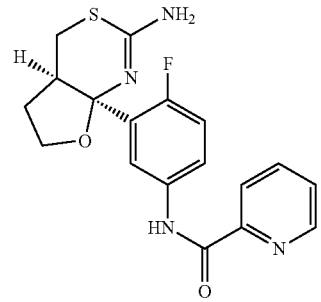 [SMILES: NC1=N[C@@]2(c3cc(NC(=O)c4ccccn4)ccc3F)OCC[C@H]2CS1]

To a solution of tert-butyl ((4aR,7aR)-7a-(2-fluoro-5-(picolinamido)phenyl)-4a,5,6,7a-tetrahydro-4H-furo[2,3-d][1,3]thiazin-2-yl)carbamate (Preparation 5, 12 mg, 0.025 mmol) in dichloromethane (254 μL) was added TFA (39.1 μL, 0.508 mmol) at rt, and the reaction mixture was stirred at rt for 3 h. The crude product was directly purified by prep TLC eluting with 90% CH2Cl2/9% MeOH/1% NH$_4$OH to give the title compound (5 mg, 0.013 mmol, 52.9% yield) a colorless oil. $^1$H NMR (500 MHz, CHLOROFORM-d) δ 10.04 (s, 1H), 8.68-8.62 (m, 1H), 8.31 (dt, J=7.8, 1.0 Hz, 1H), 8.01 (ddd, J=8.9, 4.1, 2.9 Hz, 1H), 7.93 (td, J=7.7, 1.7 Hz, 1H), 7.72 (dd, J=6.9, 2.8 Hz, 1H), 7.51 (ddd, J=7.5, 4.8, 1.1 Hz, 1H), 7.08 (dd, J=10.9, 8.8 Hz, 1H), 4.11 (t, J=7.2 Hz, 3H), 3.50 (s, 1H), 3.15 (dd, J=12.8, 4.0 Hz, 1H), 2.97 (ddd, J=13.0, 7.5, 1.8 Hz, 1H), 2.77 (dd, J=7.0, 4.0 Hz, 1H), 2.22-1.98 (m, 2H). MS (M−1): 371.2.

Example 6

N-(3-((4aR,7aR)-2-amino-4a,5,6,7a-tetrahydro-4H-furo[2,3-d][1,3]thiazin-7a-yl)-4-fluorophenyl)-5-(difluoromethoxy)picolinamide

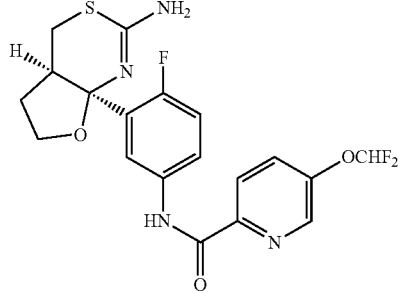 [SMILES: NC1=N[C@@]2(c3cc(NC(=O)c4ccc(OC(F)F)cn4)ccc3F)OCC[C@H]2CS1]

A solution of tert-butyl ((4aR,7aR)-7a-(5-(5-(difluoromethoxy)picolinamido)-2-fluorophenyl)-4a,5,6,7a-tetrahydro-4H-furo[2,3-d][1,3]thiazin-2-yl)carbamate (6 mg, 0.011 mmol) and TFA (17.17 μL, 0.223 mmol) in DCM (111 μL) was stirred at rt for 3 h, and the solvents were removed to give N-(3-((4aR,7aR)-2-amino-4a,5,6,7a-tetrahydro-4H- furo[2,3-d][1,3]thiazin-7a-yl)-4-fluorophenyl)-5-(difluoromethoxy)picolinamide (7 mg) as its TFA salt as a colorless oil. $^{1}$H NMR (500 MHz, METHANOL-$d_{4}$) 8.60 (br. s., 1H), 8.29 (br. s., 1H), 8.18 (dd, J=7.1, 2.7 Hz, 1H), 7.94-7.87 (m, 1H), 7.84 (dd, J=8.6, 1.6 Hz, 1H), 7.31-7.22 (m, 1H), 7.10 (t, J=75 Hz, 1H), 4.33-4.19 (m, 2H), 3.46 (dd, J=13.6, 3.8 Hz, 1H), 3.34-3.25 (m, 1H), 3.18-3.09 (m, 1H), 2.32 (q, J=7.0 Hz, 2H). MS (M+H)$^{+}$: 439.11.

Example 7

N-(3-((4aR,7aR)-2-amino-4a,5,6,7a-tetrahydro-4H-furo[2,3-d][1,3]thiazin-7a-yl)-4-fluorophenyl)-3-fluoropicolinamide

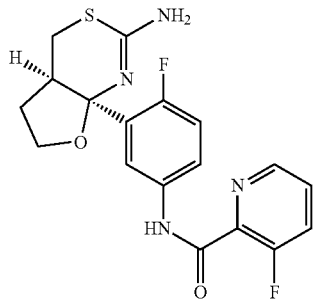 [SMILES: NC1=N[C@@]2(c3cc(NC(=O)c4ncccc4F)ccc3F)OCC[C@H]2CS1]

A solution of tert-butyl ((4aR,7aR)-7a-(2-fluoro-5-(3-fluoropicolinamido)phenyl)-4a,5,6,7a-tetrahydro-4H-furo[2,3-d][1,3]thiazin-2-yl)carbamate (6 mg, 0.012 mmol) and TFA (18.85 μL, 0.245 mmol) in DCM (122 μL) was stirred at rt for 3 h, and the solvents were removed to give N-(3-((4aR,7aR)-2-amino-4a,5,6,7a-tetrahydro-4H-furo[2,3-d][1,3]thiazin-7a-yl)-4-fluorophenyl)-3-fluoropicolinamide (7 mg) as its TFA salt as a colorless oil. $^{1}$H NMR (500 MHz, METHANOL-$d_{4}$) δ 8.84-8.37 (br. s, 2H), 8.17 (dd, J=7.2, 2.3 Hz, 1H), 7.92-7.76 (m, 2H), 7.26 (dd, J=11.1, 8.9 Hz, 1H), 4.37-4.19 (m, 2H), 3.46 (dd, J=13.6, 3.8 Hz, 1H), 3.35-3.25 (m, 1H), 3.19-3.04 (m, 1H), 2.32 (q, J=7.0 Hz, 2H). MS (M+H)$^{+}$: 391.10.

Example 8

(±)-(4aR,7aR)-7a-(2,4-difluoro-5-(5-(prop-1-ynyl)pyridin-3-yl)phenyl)-4a,5,6,7a-tetrahydro-4H-furo[2,3-d][1,3]thiazin-2-amine

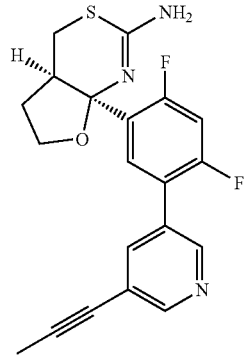 [SMILES: CC#Cc1cncc(-c2cc([C@@]34N=C(N)SC[C@@H]3CCO4)c(F)cc2F)c1]

To a solution of (±)-tert-butyl (4aR,7aR)-7a-(2,4-difluoro-5-(5-(prop-1-ynyl)pyridin-3-yl)phenyl)-4a,5,6,7a-tetrahydro-4H-furo[2,3-d][1,3]thiazin-2-ylcarbamate (Preparation 6, 22 mg) in dichloromethane (300 μL) was added TFA (35 μL, 0.508 mmol) at rt, and the reaction mixture was stirred at rt for 2.5 h. The crude product was directly purified by prep TLC eluting with 90% CH2Cl2/9% MeOH/1% NH$_{4}$OH to give the title compound (12 mg) a colorless oil. $^{1}$H NMR (400 MHz, CHLOROFORM-d) δ 8.66-8.61 (m, 2H), 7.86-7.83 (m, 1H), 7.71 (t, J=8.8 Hz, 1H), 6.98-6.91 (m, 1H), 4.15-4.03 (m, 2H), 3.15 (dd, J=13.1, 4.0 Hz, 1H), 3.00 (ddd, J=13.1, 7.5, 2.0 Hz, 1H), 2.80-2.73 (m, 1H), 2.24-2.09 (m, 5H). MS (M−1): 364.2.

Example 9

(4aR,7aR)-7a-(2-fluoro-5-(5-(prop-1-yn-1-yl)pyridin-3-yl)phenyl)-4a,5,6,7a-tetrahydro-4H-furo[2,3-d][1,3]thiazin-2-amine

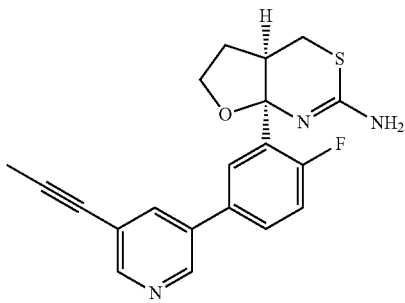 [SMILES: CC#Cc1cncc(-c2ccc(F)c([C@@]34N=C(N)SC[C@@H]3CCO4)c2)c1]

A solution of (4aR,7aR)-7a-(2-fluoro-5-(5-(prop-1-yn-1-yl)pyridin-3-yl)phenyl)-4a,5,6,7a-tetrahydro-4H-furo[2,3-d][1,3]thiazin-2-amine (23 mg, 0.063 mmol) and TFA (48.2 μL, 0.626 mmol) in DCM (417 μL) was stirred at rt for 2 h. An additional portion of TFA (38.6 μL, 0.501 mmol) was added, and the reaction mixture was stirred at rt for 1 h. The solvents were removed, and the crude product was purified by preparative TLC on silica gel (0.50 mm thickness) eluting with 90% DCM/9% MeOH/1% ammonium hydroxide to give (4aR,7aR)-7a-(2-fluoro-5-(5-(prop-1-yn-1-yl)pyridin-3-yl)phenyl)-4a,5,6,7a-tetrahydro-4H-furo[2,3-d][1,3]thiazin-2-amine (16 mg, 0.044 mmol, 69.6% yield) as a white solid. $^{1}$H NMR (500 MHz, CHLOROFORM-d) δ 8.69 (d, J=2.3 Hz, 1H), 8.59 (d, J=1.8 Hz, 1H), 7.85 (t, J=2.1 Hz, 1H), 7.82 (dd, J=7.5, 2.4 Hz, 1H), 7.45 (ddd, J=8.4, 4.4, 2.6 Hz, 1H), 7.14 (dd, J=11.0, 8.4 Hz, 1H), 4.13-4.03 (m, 2H), 3.15 (dd, J=13.0, 4.0 Hz, 1H), 2.98 (ddd, J=12.8, 7.6, 2.0 Hz, 1H), 2.84-2.72 (m, 1H), 2.23-2.15 (m, 2H), 2.12 (3H, s). MS (M+H)$^{+}$: 368.3.

Example 10

(±)-(4aR,7aR)-7a-(5-(cyclopentylamino)-2-fluorophenyl)-4a,5,6,7a-tetrahydro-4H-furo[2,3-d][1,3]thiazin-2-amine

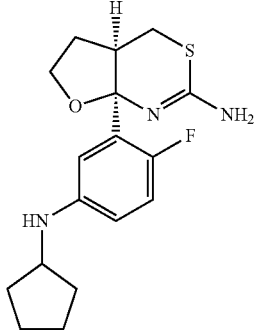 [SMILES: NC1=N[C@@]2(c3cc(NC4CCCC4)ccc3F)OCC[C@H]2CS1]

A solution of tert-butyl (±)-((4aS,7aS)-7a-(5-(cyclopentylamino)-2-fluorophenyl)-4a,5,6,7a-tetrahydro-4H-furo[2,3-d][1,3]thiazin-2-yl)carbamate (16 mg, 0.037 mmol) and TFA (56.6 µL, 0.735 mmol) in DCM (245 µL) was stirred at rt for 3 h. The solvents were removed to give (4aS,7aS)-7a-(5-(cyclopentylamino)-2-fluorophenyl)-4a,5,6,7a-tetrahydro-4H-furo[2,3-d][1,3]thiazin-2-amine (17 mg) as its TFA salt as a colorless oil. MS (M+H)$^+$: 336.02.

Example 11

(4aR,8aR)-8a-(2,4-difluoro-5-(pyrimidin-5-yl)phenyl)-4,4a,5,6,7,8a-hexahydropyrano[2,3-d][1,3]thiazin-2-amine

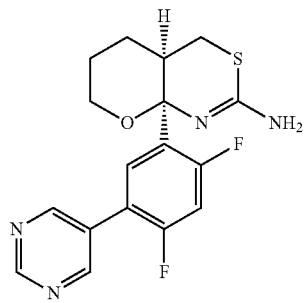 [SMILES: NC1=N[C@@]2(c3cc(-c4cncnc4)c(F)cc3F)OCCC[C@H]2CS1]

To a solution of 5-((tert-butyldimethylsilyl)oxy)-1-(2,4-difluoro-5-(pyrimidin-5-yl)phenyl)-2-methylenepentan-1-one (Preparation 16, 606 mg, 1.448 mmol) in HOAc (7239 µL) was added thiourea (441 mg, 5.79 mmol), and a suspension was formed. The reaction mixture was stirred at rt for 12 h, and a clear yellowish solution was formed. TBAF (2172 µL, 2.172 mmol) in THF was added, and the reaction mixture was stirred at rt for 5 h, followed by heating at 60° C. for 12 h. This crude reaction mixture was purified by reverse phase preparative HPLC on a Luna C18 column (10 µM, 30×100 mm) eluting with 0-100% B (A: 10% MeOH/90% water/0.1% TFA; B: 90% MeOH/10% water/0.1% TFA) over 12 min to give a mixture of two isomers. This mixture was purified by preparative TLC on silica gel (0.50 mm thickness) eluting with 90% DCM/9% MeOH/1% ammonium hydroxide to give (4aS,8aS)-8a-(2,4-difluoro-5-(pyrimidin-5-yl)phenyl)-4,4a,5,6,7,8a-hexahydropyrano[2,3-d][1,3]thiazin-2-amine (13 mg, 0.034 mmol, 2.354% yield) as a white solid. $^1$H NMR (500 MHz, CHLOROFORM-d) δ 9.22 (s, 1H), 8.91 (d, J=1.4 Hz, 2H), 7.43 (t, J=8.5 Hz, 1H), 7.02 (dd, J=10.8, 10.2 Hz, 1H), 5.0-4.5 (broad s, 2H), 4.00-3.92 (m, 1H), 3.88-3.80 (m, 1H), 2.95 (dd, J=12.6, 4.0 Hz, 1H), 2.81-2.71 (m, 1H), 2.67 (dd, J=12.6, 2.8 Hz, 1H), 2.01-1.83 (m, 2H), 1.75-1.57 (m, 2H). MS (M+H)$^+$: 363.03.

Biological Methods

Cellular Assays for Inhibition of Aβ1-40 and Aβ1-42 Production

H4 cells stably transfected with APP751 containing the Swedish mutation (H4 APP751 SWE clone 8.20, developed at BMS) were maintained in log phase through twice weekly passage at a 1:20 split. For IC$_{50}$ determinations, 30 µl cells (1.5×10$^4$ cells/well) in DMEM media containing 0.0125% BSA (Sigma A8412) were plated directly into 384-well compound plates (Costar 3709) containing 0.1 µl serially diluted compound in DMSO. Following incubation for 19 h in 5% CO$_2$ at 37° C., plates were briefly centrifuged (1000 rpm, 5 min). A 10 µl aliquot from each well was transferred to a second assay plate (Costar 3709) for Aβ40 measurements. Antibody cocktails were freshly prepared by dilution into 40 mM Tris-HCl (pH 7.4) with 0.2% BSA and added to assay plates. For Aβ42 measurements, antibodies specific for the Aβ42 neoepitope (565, developed at BMS; conjugated to the Wallac reagent (Perkin Elmer)) and the N-terminal sequence of Aβ peptide (26D6, developed at SIBIA; conjugated to APC (Perkin Elmer)) were mixed and 20 µl of the mixture was added to each well of the incubated cell plate yielding a final concentration of 0.8 ng/well 565 and 75 ng/well 26D6. For the Aβ40 measurements, antibodies specific for the Aβ40 neoepitope (TSD, developed at BMS; conjugated to the Wallac reagent (Perkin Elmer)) and 26D6 as described above were mixed and 20 µl of the mixture was added to the 10 µl aliquots which had been removed previously from the cell plate yielding a final concentration of 1.6 ng/well TSD and 17.5 ng/well 26D6. Assay plates containing antibodies were sealed with aluminum foil and incubated overnight at 4° C. Signal was determined using a Viewlux counter (Perkin Elmer) and IC$_{50}$ values determined using curve fitting in CurveMaster (Excel Fit based).

The activity of representative compounds of the present disclosure, based on Aβ42 cellular IC$_{50}$ values in H4 APP751 SWE clone 8.20, are illustrated below in Table 1.

TABLE 1

| Cellular activity of examples | |
| --- | --- |
| Example # | IC$_{50}$ |
| 1 | 34 nM |
| 2 | 24 nM |
| 3 | 72 nM |
| 4 | 465 nM |
| 5 | 856 nM |
| 8 | 924 nM |
| 11 | 995 nM |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:
1. A compound of formula (I), including pharmaceutically acceptable salts thereof:

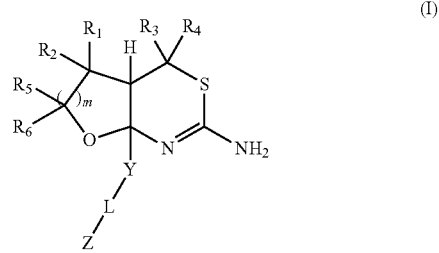

wherein R$_1$, R$_2$, R$_3$, R$_4$, R$_5$, and R$_6$ are independently hydrogen, C$_1$-C$_6$ alkyl or C$_1$-C$_6$ cycloalkyl;

Y and Z are independently a $C_6$-$C_{10}$-aryl group or a 5-10 membered heterocyclic group, wherein each Y and Z group can be further substituted with from 0-3 substituents selected from halogen, amino, $C_{1-4}$alkylamino, $C_{1-4}$dialkylamino, halo$C_{1-4}$ alkyl, OH, CN, $C_1$-$C_6$ alkyl or cycloalkyl, $C_1$-$C_6$ alkoxy, and $C_2$-$C_4$ alkynyl;

L is either a bond or is —NHCO—;

L and Z together can be absent; and m is 1, 2 or 3.

2. The compound of claim 1, wherein:

$R_1$, $R_2$, $R_3$, $R_4$, $R_5$, and $R_6$ are independently hydrogen, $C_1$-$C_6$ alkyl or $C_1$-$C_6$ cycloalkyl;

Y is phenyl or thiophenyl and Z is a pyridyl, pyrimidinyl or pyrazinyl, wherein each Y and Z group can be optionally substituted with from 0-3 substituents selected from hydrogen, halogen, amino, $C_{1-4}$alkylamino, $C_{1-4}$dialkylamino, halo$C_{1-4}$ alkyl, OH, CN, $C_1$-$C_6$ alkyl or cycloalkyl, $C_1$-$C_6$ alkoxy, or $C_2$-$C_4$ alkynyl;

L is either a bond or is —NHCO—; and m is 1 or 2.

3. The compound of claim 2, wherein:

$R_1$, $R_2$, $R_3$, $R_4$, $R_5$, and $R_6$ are hydrogen;

Y is phenyl and Z is a pyridyl, wherein each Y and Z group can be optionally substituted with from 0-3 halogen substituents and Z can be optionally substituted with from 0-3 halogen, cyano, or $C_2$-$C_4$ alkynyl substituents;

L is either a bond or is —NHCO—; and m is 1 or 2.

4. The compound of claim 2, wherein:

$R_1$, $R_2$, $R_3$, $R_4$, $R_5$, and $R_6$ are hydrogen;

Y is phenyl optionally substituted with from 0-3 halogen, cyano, or $C_2$-$C_4$ alkynyl substituents;

L and Z together can be absent; and m is 1 or 2.

5. A compound of any claims of 1 to 3, wherein the configuration of the chiral center adjacent to the nitrogen of the aminothiazine is (R) or a pharmaceutically acceptable salt thereof.

6. The compound of claim 4, which is selected from the group consisting of:

N-(3-((4aR,7aR)-2-amino-4-a,5,6,7a-tetrahydro-4H-furo[2,3-d][1,3]thiazin-7a-yl)-4-fluorophenyl)-5-chloropicolinamide;

N-(3-((4aR,7aR)-2-amino-4-a,5,6,7a-tetrahydro-4H-furo[2,3-d][1,3]thiazin-7a-yl)-4-cyanophenyl)-5-chloropicolinamide;

N-(3-((4aR,7aR)-2-amino-4-a,5,6,7a-tetrahydro-4H-furo[2,3-d][1,3]thiazin-7a-yl)-4-cyanophenyl)-5-bromopicolinamide;

N-(3-((4aR,7aR)-2-amino-4a,5,6,7a-tetrahydro-4H-furo[2,3-d][1,3]thiazin-7a-yl)-4-fluorophenyl)-5-(difluoromethoxy)picolinamide;

N-(3-((4aR,8aR)-2-amino-4,4a,5,6,7,8a-hexahydropyrano[2,3-d][1,3]thiazin-8a-yl)-4-fluorophenyl)-5-(difluoromethoxy)picolinamide;

N-(3-((4aR,8aR)-2-amino-4,4a,5,6,7,8a-hexahydropyrano[2,3-d][1,3]thiazin-8a-yl)-4-fluorophenyl)-5-chloropicolinamide;

N-(3-((4aR,8aR)-2-amino-4,4a,5,6,7,8a-hexahydropyrano[2,3-d][1,3]thiazin-8a-yl)-4-fluorophenyl)-5-bromopicolinamide;

N-(3-((4aR,8aR)-2-amino-4,4a,5,6,7,8a-hexahydropyrano[2,3-d][1,3]thiazin-8a-yl)-4-fluorophenyl)-5-cyanopicolinamide; and N-(3-((4aR,8aR)-2-amino-4,4a,5,6,7,8a-hexahydropyrano[2,3-d][1,3]thiazin-8a-yl)-4-fluorophenyl)-5-fluoropicolinamide;

or a pharmaceutically acceptable salt thereof.

7. A pharmaceutical composition which comprises one or more of the compounds as claimed in claim 1, together with one or more pharmaceutically acceptable carriers, excipients or diluents.

8. A pharmaceutical composition which comprises one or more of the compounds as claimed in claim 4, together with one or more pharmaceutically acceptable carriers, excipients or diluents.

9. A pharmaceutical composition which comprises one or more of the compounds as claimed in claim 5, together with one or more pharmaceutically acceptable carriers, excipients or diluents.

* * * * *